United States Patent
Korchia-Maor et al.

(10) Patent No.: US 11,918,013 B2
(45) Date of Patent: Mar. 5, 2024

(54) COMPOSITION FOR INACTIVATION OF GRAM-POSITIVE BACTERIA AND BACTERIAL SPORES AND METHODS OF MAKING AND USING SAME

(71) Applicant: RESORCIX LTD., Jerusalem (IL)

(72) Inventors: Yehoshua Korchia-Maor, Jerusalem (IL); Lior Sinai, Jerusalem (IL)

(73) Assignee: RESORCIX LTD., Jerusalem (IL)

( * ) Notice: Subject to any disclaimer, the term of this patent is extended or adjusted under 35 U.S.C. 154(b) by 613 days.

(21) Appl. No.: 17/259,169

(22) PCT Filed: Jul. 10, 2019

(86) PCT No.: PCT/IB2019/000659
§ 371 (c)(1),
(2) Date: Jan. 10, 2021

(87) PCT Pub. No.: WO2020/012242
PCT Pub. Date: Jan. 16, 2020

(65) Prior Publication Data
US 2021/0153525 A1    May 27, 2021

Related U.S. Application Data

(60) Provisional application No. 62/695,867, filed on Jul. 10, 2018.

(51) Int. Cl.
| | | |
|---|---|---|
| A23L 33/105 | (2016.01) |
| A23L 2/02 | (2006.01) |
| A23L 2/44 | (2006.01) |
| A23L 2/68 | (2006.01) |
| A23L 3/3472 | (2006.01) |
| A23L 3/3508 | (2006.01) |

(52) U.S. Cl.
CPC .................. *A23L 2/44* (2013.01); *A23L 2/02* (2013.01); *A23L 2/68* (2013.01); *A23L 3/3472* (2013.01); *A23L 3/3508* (2013.01); *A23L 33/105* (2016.08)

(58) Field of Classification Search
CPC ..... A23L 2/02; A23L 2/44; A23L 2/68; A23L 33/105; A23L 3/3472; A23L 3/3508
See application file for complete search history.

(56) References Cited

U.S. PATENT DOCUMENTS

| 10,415,001 B2 | 9/2019 | Dilk et al. |
| 2013/0280392 A1 | 10/2013 | Semenza |
| 2019/0151232 A1* | 5/2019 | Scharp ................. A61K 31/245 |

FOREIGN PATENT DOCUMENTS

| CN | 106726870 | * | 5/2017 |
| JP | 08012560 | * | 1/1996 |
| WO | 2005/110446 A1 | | 11/2005 |

OTHER PUBLICATIONS

Plants for a Future. 2017. https://web.archive.org/web/20170820181230/https://pfaf.org/user/Plant.aspx?Latin Name=Copaifera+officinalis. *

(Continued)

*Primary Examiner* — Anthony J Weier
(74) *Attorney, Agent, or Firm* — Daniel Feigelson

(57) ABSTRACT

There are provided compositions for inactivation of Gram-positive bacteria and bacterial spores, and methods of making and using such compositions. The compositions may contain 7-alpha-acetoxyhardwickiic acid, crolechinic acid, hardwickiic acid, kolavenic acid and copalic acid.

20 Claims, 9 Drawing Sheets

(56) References Cited

OTHER PUBLICATIONS

Braga et al., "Terpenoids From Copaiba Cearensis", Phytochemistry, vol. 49, No. 1, pp. 263-264, 1998.
Cai et al., "Diterpenes From Croton Lechleri", Phytochemistry, 32(3), pp. 755-760 (1993).
Costa et al., "Synthesis of methyl dihydrohardwickiate and its C-4 epimer. Structural amendment of natural crolechinic acid", Phytochemistry 53 (2000) 851-854.
Santos et al., "Antimicrobial activity of Amazonian oils against *paenibacillus* species", Journal of Invertebrate Pathology 109 (2012) 265-268.
Pinto et al., "Separation of Acid Diterpenes of Copaifera cearensis Huber ex Ducke by Flash Chromatography Using Potassium Hydroxide Impregnated Silica Gel", J. Braz. Chem. Soc., vol. 11, No. 4, 355-360, 2000.
Morelli et al., "Natural copaiba oil as antibacterial agent for bio-based active packaging", Industrial Crops and Products 70 (2015) 134-141.
Kuete et al., "Antimicrobial activity of the methanolic extract, fractions and compounds from the stem bark of Irvingia gabonensis (Ixonanthaceae)", Journal of Ethnopharmacology 114 (2007) 54-60.
Leandro et al., "Chemistry and Biological Activities of Terpenoids from Copaiba (*Copaifera* spp.) Oleoresins", Molecules 2012, 17, 3866-3889; doi: 10.3390/molecules17043866.
McChesney et al., "Antimicrobial terpenes of Croton sonderianus 1. Hardwickic and 3,4-Secotrachylobanoic acids", Journal of Natural Products, 54(6) pp. 1625-1633, 1991.
Nogueira et al., "Clerodane-type diterpenes from the seed pods of *Hymenaea courbaril* var. *stilbocarpa*", Phytochemistry 58 (2001) 1153-1157.
Souza et al., "Antimicrobial Evaluation of Diterpenes from Copaifera langsdorffii Oleoresin Against Periodontal Anaerobic Bacteria", Molecules 2011, 16, 9611-9619; doi:10.3390/molecules16119611.
Souza et al., "Antimicrobial Activity of Terpenoids from Copaifera langsdorffii Desf. Against Cariogenic Bacteriaptr_3244 215", Phytother. Res. 25: 215-220 (2011).
Spanevello et al., "7-alpha-acetoxyhardwickiic acid: a furanoid clerodane", Phytochemistry 35(2) pp. 537-538, 1994.
Tincusi et al., "Antimicrobial Terpenoids from the Oleoresin of the Peruvian Medicinal Plant Copaifera paupera", Planta Med 2002; 68: 808-812.
Trinidade et al., "Copaifera of the Neotropics: A Review of the Phytochemistry and Pharmacology", Int. J. Mol. Sci. 2018, 19, 1511; doi:10.3390/ijms19051511.
Veiga Junior et al., "Chemical composition and anti-inflammatory activity of copaiba oils from Copaifera cearensis Huber ex Ducke, Copaifera reticulata Ducke and Copaifera multijuga Hayne—A comparative study", Journal of Ethnopharmacology 112 (2007) 248-254.
Xavier-Junior et al., "Development of a Gas Chromatography Method for the Analysis of Copaiba Oil", Journal of Chromatographic Science, 2017, vol. 55, No. 10, 969-978, doi: 10.1093/chromsci/bmx065.
Lemos et al., "Copaifera langsdorffii: Evaluation of potential gastroprotective of extract and isolated compounds obtained from leaves". Brazilian Journal of Pharmacognosy 2015, 25, 238-245, http://dx.doi.org/10.1016/j.bjp.2015.05.005.

* cited by examiner

COMPOSITION FOR INACTIVATION OF GRAM-POSITIVE BACTERIA AND BACTERIAL SPORES AND METHODS OF MAKING AND USING SAME

CROSS-REFERENCE TO RELATED APPLICATION

This application claims priority from, and the benefit of, U.S. Provisional Application No. 62/695,867, filed Jul. 10, 2019. The contents of this application are incorporated herein by reference.

BACKGROUND

Gram-positive bacteria are a potential threat as they are associated with human diseases and food spoilage. Certain genera of Gram-positive bacteria, such as *Bacillus* and *Clostridium* can form highly resistant, and dormant, structures called spores. The unique characteristics of spores make them the potential sole surviving and growing contaminants in specific industrially processed foods such as pasteurized food products. For example, *Alicyclobacillus* spp spores are the only organisms that survive pasteurization of fruit juices, and that are capable of growing in the acidic pH environment of such juices. Besides causing food spoilage, Gram-positive bacteria can also be pathogenic to humans. *Listeria monocytogenes, Staphylococcus aureus* and the spore-formers, *Bacillus cereus* and *Clostridium botulinum*, are significant threats for the food industry.

DESCRIPTION

The present inventors have found that a particular composition prepared from resin obtained from species of the plant *Copaifera* is capable of controlling not only Gram-positive bacteria generally, but also, surprisingly, to control the growth of spores of such bacteria. Moreover, unlike resins obtained from *Copaifera* species, which are unsuitable for use in the food production industry because they impart a bitter taste to foods, the presently claimed compositions can be used, for example, to control Gram-positive bacteria, including spore-producing Gram-positive bacteria, without imparting such a taste. This composition, its production and use is described in greater detail below.

The composition claimed herein has been found to kill Gram-positive bacteria associated with food spoilage, including Gram-positive pathogens such as *Listeria monocytogenes, Bacillus cereus*, and Methicillin-resistant *Staphylococcus aureus* (MRSA). The composition has also been found to kill Gram-positive bacteria in the form of spores. Spore-forming bacteria represent particular problems for the food industry. There is a clear association between soil-borne spore-forming bacteria and food contamination. The spore formers implicated belong both to the strictly anaerobic ("the Clostridia") and to the aerobic (the genus *Bacillus* and related genera) phylogenetic groups of microorganisms. Several reasons have been proposed to explain why spore formers have become a problem in the food industry, and most explanations are related to some general characteristics of the spores: their ubiquitous presence in soil; their resistance to heat in common industrial processes such as pasteurization; the adhesive characters of particular spores that facilitate their attachment to processing equipment, and/or their ability to germinate and grow in favorable conditions. The concerted characteristics of spores and vegetative cells of particular soil-borne species make them potential sole surviving and growing contaminants in specific industrially processed foods. Some of them have only become a concern recently, which might be the result of increasing tolerance, adaptation, or resistance of spores or vegetative cells of particular spore-forming species to conditions or treatments that were previously presumed either to stop growth (low temperatures and low pH) or to inactivate all living material (ultrahigh heat treatment (UHT) and commercial sterilization).

Spore forming bacteria cause two kinds of problems in the food industry. First, they may be food-borne pathogens such as *Bacillus cereus* and *Clostridium botulinum*. Second, even if such spore-forming bacteria are not themselves pathogens, they may cause a reduction of shelf life and food spoilage. Microbial spoilage of food is usually indicated by changes in texture or the development of off-flavors. A relevant example is spores of *Alicyclobacillus*, a genus of spoilage bacteria causing contamination of juices and other beverage products that cannot easily be contaminated by other microbes because of their high acid contents. During the five decades since the first species of *Alicyclobacillus* was isolated in 1967, *Alicyclobacillus* has become a significant concern to the global juice and beverage industries. These spore-forming bacteria can survive commercially used pasteurization procedures, and can germinate in an acid environment. To date, this kind of bacterium has been isolated from many kinds of juice and beverage products and nearly all segments of juice and beverage production lines. Today, the demands for safe and high-quality juice and beverage products continue to increase at a fast pace worldwide. However, with the development of juice and beverage manufacturers especially, *Alicyclobacillus* contamination has become a significant concern and challenge. Spoilage of fruit juice by *Alicyclobacillus* is characterized by a distinct medicinal or antiseptic off-odor attributed to guaiacol, a metabolic by-product of the bacterium.

Both pathogenic and spoilage bacteria can occur in raw food materials, but heat processing tends to reduce bacterial loads dramatically. Subsequent to processing, most foods are at risk for recontamination prior to packaging, distribution, and final consumption, when the foods may be exposed to pathogens in the food handling environment. In the case of cold tolerant pathogens, mainly various *Listeria* and *Bacillus cereus* species, they may then grow on the food during distribution and storage until final consumption. The more such pathogens grow in a food product, the higher the risk of infection among consumers of that food product. This is a particular concern for ready-to-eat meats and dairy products, as such foods are not heated or processed again by the user before consumption. In such cases, the most likely risk is from *Listeria* species that grow well under refrigeration.

There is provided, in accordance with an embodiment of the invention, a composition of matter comprising (a) crolechinic acid, hardwickiic acid, kolavenic acid, copalic acid, and, optionally, 7-alpha-acetoxyhardwickiic acid, and (b) optionally, beta-caryophyllene (BCP), the ratio of said crolechinic acid, hardwickiic acid, kolavenic acid, copalic acid, and 7-alpha-acetoxyhardwickiic acid if present, taken together, to said beta-caryophyllene, when beta-caryophyllene is present, being at least 1:1 by weight. In some embodiments the composition comprises 7-alpha-acetoxyhardwickiic acid. In some embodiments the composition is substantially free of BCP.

In some embodiments, the ratio of the crolechinic acid, hardwickiic acid, kolavenic acid, copalic acid, and 7-alpha-acetoxyhardwickiic acid, if present, taken together, to the beta-caryophyllene is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7, at least 2.8, at least 2.9:1, or at least 3.0:1 by weight.

In some embodiments, the ratio of the crolechinic acid, hardwickiic acid, kolavenic acid, copalic acid, and 7-alpha-acetoxyhardwickiic acid, if present, taken together, to the beta-caryophyllene is not greater than 100:1 by weight. In some embodiments the ratio of said crolechinic acid, hardwickiic acid, kolavenic acid, copalic acid and 7-alpha-acetoxyhardwickiic acid, if present, taken together, to said beta-caryophyllene is not greater than 90:1, not greater than 80:1, not greater than 70:1, not greater than 60:1, not greater than 50:1, not greater than 40:1 not greater than 30:1, not greater than 20:1, not greater than 10:1, not greater than 9:1, not greater than 8:1, not greater than 7:1, not greater than 6:1, not greater than 5:1, not greater than 4:1, or not greater than 3:1 by weight.

In some embodiments, 7-alpha-acetoxyhardwickiic acid constitutes at least 7 wt. % of the amount of 7-alpha-acetoxyhardwickiic acid, crolechinic acid, hardwickiic acid, kolavenic acid and copalic acid taken together. In some embodiments, 7-alpha-acetoxyhardwickiic acid constitutes at least 10 wt. % of the amount of 7-alpha-acetoxyhardwickiic acid, crolechinic acid, hardwickiic acid, kolavenic acid and copalic acid taken together.

In some embodiments, the composition is active against spores of *Alicyclobacillus*.

In some embodiments, the composition is substantially free of hexane and dichloromethane.

There is also provided, in accordance with an embodiment of the invention, a method of preparing a composition as recited above, which composition has, relative to the concentration of 7-alpha-acetoxyhardwickiic acid, crolechinic acid, hardwickiic acid, kolavenic acid and copalic acid taken together in copaiba resin obtained from *Copaifera*, a reduced concentration of beta-caryophyllene (BCP), the method comprising extracting resin obtained from *Copaifera* with a mixture of water and ethanol, and collecting the upper fraction obtained from the extraction, whereby to obtain the composition. In some embodiments, the composition is active against spores of *Alicyclobacillus*.

In some embodiments, the copaiba resin is obtained from *Copaifera officinalis*.

In some embodiments, the composition is active against spores of *Alicyclobacillus* acidoterrestris.

In some embodiments, the ratio of ethanol to water in the mixture is at least 1:1 by weight. In some embodiments, the ratio of ethanol to water in the mixture is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7:1, at least 2.8:1, at least 2.9:1, or at least 3:1 by weight.

In some embodiments, the ratio of ethanol to water in the mixture is not more than 4:1, not more than 3.9:1, not more than 3.8:1, not more than 3.7:1, not more than 3.6:1, not more than 3.5:1, not more than 3.4:1, not more than 3.3:1, not more than 3.2:1, or not more than 3.1:1 by weight.

In some embodiments, the mixture of ethanol and water contains NaOH in a concentration of 0.01 to 0.125 molar. In some embodiments the concentration of NaOH is at least 0.02 M, at least 0.03 M, at least 0.04 M, at least 0.05 M, at least 0.06 M, at least 0.07 M, at least 0.08 M, at least 0.09 M, at least 1.0 M, at least 1.1 M or at least 1.2 M.

In some embodiments, the mixture of ethanol and water contains HCl in a concentration of 0.01 to 0.25 molar. In some embodiments, the concentration of HCl is at least 0.1 molar, at least 0.2 molar, at least 0.3 molar, at least 0.4 molar, at least 0.5 molar, at least 0.6 molar, at least 0.7 molar, at least 0.8 molar, at least 0.9 molar, at least 1.0 molar, at least 1.1 molar, at least 1.2 molar, or at least 0.125 molar.

In some embodiments, the ratio of the mixture of ethanol and water to copaiba resin is at least 3:1 by weight.

In some embodiments, the ratio of the mixture of ethanol and water to copaiba resin is at least 3.5:1, at least 4:1, at least 4.5:1, at least 5:1, at least 5.5:1 or at least 6:1 by weight.

In some embodiments, the method further comprises removing at least some of the water and ethanol from the collected upper fraction.

In some embodiments, the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (when present), crolechinic acid, hardwickiic acid, kolavenic acid and copalic acid, taken together, to said BCP in said upper fraction is at least 1:1 by weight. In some embodiments, the ratio of said 7-alpha-acetoxyhardwickiic acid, crolechinic acid, hardwickiic acid, kolavenic acid and copalic acid, taken together, to said BCP in said upper fraction is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1 or at least 2.5:1 by weight.

In some embodiments, the method further comprises chromatographically separating residual BCP from the diterpenes present in the upper fraction and collecting the diterpenes.

There is also provided, in accordance with an embodiment of the invention, a method of preparing a composition which is active against spores of *Alicyclobacillus* and has a reduced concentration of beta-caryophyllene (BCP) relative to the concentration of BCP in copaiba resin obtained from *Copaifera*, the method comprising extracting resin obtained from *Copaifera* with a mixture of water and ethanol, and collecting the upper fraction obtained from the extraction. In this context, the term "active against spores of *Alicyclobacillus*" means that, when added at a concentration of 5 μg/ml to a sample of apple juice having a turbidity of not more than 1 Nephelometric Turbidity Units (NTU) as measured in accordance with EPA standard 180.1 (published August 1993), and containing $10^4$ spores of *Alicyclobacillus*/ml and maintained thereafter at 37° C., the composition prevents regrowth of *Alicyclobacillus* for at least four days, as determined by optical density measurement at 600 nm.

In some embodiments, the copaiba resin is obtained from *Copaifera officinalis*.

In some embodiments, the composition is active against spores of *Alicyclobacillus* acidoterrestris.

In some embodiments, the ratio of ethanol to water in the mixture is at least 1:1 by weight. In some embodiments, the ratio of ethanol to water in the mixture is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3.1, at least 2.4:1, at least 2.5:1, at least 2.6:1, at least 2.7:1, at least 2.8:1, at least 2.9:1, or at least 3:1 by weight.

In some embodiments, the ratio of ethanol to water in the mixture is not more than 4:1, not more than 3.9:1, not more than 3.8:1, not more than 3.7:1, not more than 3.6:1, not more than 3.5:1, not more than 3.4:1, not more than 3.3:1, not more than 3.2:1, or not more than 3.1:1 by weight.

In some embodiments, the mixture of ethanol and water contains NaOH in a concentration of 0.01 to 0.125 molar. In some embodiments the concentration of NaOH is at least 0.02 M, at least 0.03 M, at least 0.04 M, at least 0.05 M, at least 0.06 M, at least 0.07 M, at least 0.08 M, at least 0.09 M, at least 1.0 M, at least 1.1 M or at least 1.2 M.

In some embodiments, the mixture of ethanol and water contains HCl in a concentration of 0.01 to 0.25 molar. In some embodiments, the concentration of HCl is at least 0.1 molar, at least 0.2 molar, at least 0.3 molar, at least 0.4 molar, at least 0.5 molar, at least 0.6 molar, at least 0.7 molar, at least 0.8 molar, at least 0.9 molar, at least 1.0 molar, at least 1.1 molar, at least 1.2 molar, or at least 0.125 molar.

In some embodiments, the ratio of the mixture of ethanol and water to copaiba resin is at least 3:1 by weight.

In some embodiments, the ratio of the mixture of ethanol and water to copaiba resin is at least 3.5:1, at least 4:1, at least 4.5:1, at least 5:1, at least 5.5:1 or at least 6:1 by weight.

In some embodiments, the method further comprises removing at least some of the water and ethanol from the collected upper fraction.

In some embodiments, the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (if present), crolechinic acid, hardwickiic acid, kolavenic acid and copalic acid, taken together, to said BCP in said upper fraction is at least 1:1 by weight. In some embodiments, the ratio of said 7-alpha-acetoxyhardwickiic acid (if present), crolechinic acid, hardwickiic acid, kolavenic acid and copalic acid, taken together, to said BCP in said upper fraction is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1 or at least 2.5:1 by weight.

In some embodiments, the method further comprises chromatographically separating residual BCP from the diterpenes present in the upper fraction and collecting the diterpenes.

There is also provided, in accordance with an embodiment of the invention, a composition of matter, prepared by extraction as described herein, i.e. by a method comprising extracting resin obtained from *Copaifera* with a mixture of water and ethanol, and collecting the upper fraction obtained from the extraction, hi some embodiments, the composition is active against spores of *Alicyclobacillus*. In some embodiments, the composition has a reduced concentration of beta-caryophyllene (BCP) relative to the concentration of BCP in copaiba resin obtained from *Copaifera*. In some embodiments, the copaiba resin is obtained from *Copaifera officinalis*.

In some embodiments, the composition is active against spores of *Alicyclobacillus* acidoterrestris.

In some embodiments, the ratio of ethanol to water in the mixture is at least 1:1 by weight. In some embodiments, the ratio of ethanol to water in the mixture is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7:1, at least 2.8:1, at least 2.9:1, or at least 3:1 by weight.

In some embodiments, the ratio of ethanol to water in the mixture is not more than 4:1, not more than 3.9:1, not more than 3.8:1, not more than 3.7:1, not more than 3.6:1, not more than 3.5:1, not more than 3.4:1, not more than 3.3:1, not more than 3.2:1, or not more than 3.1:1 by weight.

In some embodiments, the mixture of ethanol and water contains NaOH in a concentration of 0.01 to 0.125 molar. In some embodiments the concentration of NaOH is at least 0.02 M, at least 0.03 M, at least 0.04 M, at least 0.05 M, at least 0.06 M, at least 0.07 M, at least 0.08 M, at least 0.09 M, at least 1.0 M, at least 1.1 M or at least 1.2 M.

In some embodiments, the mixture of ethanol and water contains HCl in a concentration of 0.01 to 0.25 molar. In some embodiments, the concentration of HCl is at least 0.1 molar, at least 0.2 molar, at least 0.3 molar, at least 0.4 molar, at least 0.5 molar, at least 0.6 molar, at least 0.7 molar, at least 0.8 molar, at least 0.9 molar, at least 1.0 molar, at least 1.1 molar, at least 1.2 molar, or at least 0.125 molar.

In some embodiments, the ratio of the mixture of ethanol and water to copaiba resin is at least 3:1 by weight.

In some embodiments, the ratio of the mixture of ethanol and water to copaiba resin is at least 3.5:1, at least 4:1, at least 4.5:1, at least 5:1, at least 5.5:1 or at least 6:1 by weight.

In some embodiments, the method further comprises removing at least some of the water and ethanol from the collected upper fraction.

In some embodiments, the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (if present), crolechinic acid, hardwickiic acid, kolavenic acid and copalic acid, taken together, to said BCP in said upper fraction is at least 1:1 by weight. In some embodiments, the ratio of said 7-alpha-acetoxyhardwickiic acid (if present), crolechinic acid, hardwickiic acid, kolavenic acid and copalic acid, taken together, to said BCP in said upper fraction is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1 or at least 2.5:1 by weight.

In some embodiments, the method further comprises chromatographic-ally separating residual BCP from the diterpenes present in the upper fraction and collecting the diterpenes.

There is also provided, in accordance with an embodiment, of the invention, a method the method comprising adding to a beverage a composition comprising (a) crolechinic acid, hardwickiic acid, kolavenic acid and copalic acid, and, optionally, 7-alpha-acetoxyhardwickiic acid, and (b) optionally, beta-caryophyllene, as described herein. In some embodiments, the beverage has a turbidity of not more than 5 Nephelometric Turbidity Units (NTU), as measured in accordance with the United States Environmental Protection Agency Method no. 180.1, published August 1993. In some embodiments, the beverage has a turbidity of not more than 4 NTU. In some embodiments, the beverage has a turbidity of not more than 3 NTU. In some embodiments, the beverage has a turbidity of not more than 2 NTU. In some embodiments, the beverage has a turbidity of not more than 1 NTU. In some embodiments, the method is for enhancing the efficacy of pasteurization of the beverage. In some embodiments, the composition is active against spores of *Alicyclobacillus*, In some embodiments, the composition is active against spores of *Alicyclobacillus acidoterrestris*. In some embodiments the composition has a reduced concentration of beta-caryophyllene (BCP) relative to the concentration of BCP in copaiba resin obtained from *Copaifera*. In some embodiments the copaiba resin is from *Copaifera officinalis*. In some embodiments, the ratio of 7-alphaacetoxyhardwickiic acid (if present), crolechinic acid, hardwickiic acid, kolavenic acid and copalic acid, taken together, to the beta-caryophyllene, when beta-caryophyllene is present, is at least 1:1 by weight. In some embodiments, the composition is added to the beverage at concentration of at least 1.25 microgram composition per ml beverage. In some embodiments, the composition is added to the beverage at a concentration of at least 2.5 microgram composition per ml beverage. In some embodiments, the composition is added to the beverage at a concentration of at least 3.75 microgram composition per ml beverage. In some embodiments, the composition is added to the beverage at a concentration of at least 5.0 microgram composition per ml beverage. In some embodiments, the composition is added to the beverage at a concentration of not more than 5.0 microgram composition per ml beverage. In some embodiments, the composition is allowed to contact the beverage for at least two days, at least three days, at least four days, or at least five days. In some embodiments, the composition is added to the beverage prior to pasteurization. In some embodiments, the composition is added to the beverage after pasteurization. In some embodiments the beverage is acidic. In some embodiments the beverage has a pH in the range of 3 to 6. In some embodiments the beverage is a fruit juice. In some embodiments the fruit juice is apple juice.

In some embodiments the fruit juice is grape juice. In some embodiments the fruit juice is peach juice. In some embodiments the fruit juice is watermelon juice. In some embodiments the fruit juice is clear orange juice. In some embodiments, the composition is a composition as described above. In some embodiments, the composition has been prepared by a method as described hereinabove.

There is also provided, in accordance with an embodiment of the invention, a method comprising adding to a beverage a composition which has been prepared by extracting *Copaifera* resin with a mixture of water and ethanol, and collecting the upper fraction obtained from the extraction to obtain the composition. In some embodiments, the beverage has a turbidity of not more than 5 Nephelometric Turbidity Units (NTU), as measured in accordance with the United States Environmental Protection Agency Method no. 180.1, published August 1993. In some embodiments, the beverage has a turbidity of not more than 4 NTU. In some embodiments, the beverage has a turbidity of not more than 3 NTU. In some embodiments, the beverage has a turbidity of not more than 2 NTU. In some embodiments, the beverage has a turbidity of not more than 1 NTU. In some embodiments, the method is for enhancing the efficacy of pasteurization of the beverage. In some embodiments, the method is for controlling the growth of Gram-positive bacteria, including spores of Gram-positive bacteria, in the beverage. In some embodiments, the composition is active against spores of *Alicyclobacillus acidoterrestris*. In some embodiments the composition has a reduced concentration of beta-caryophyllene (BCP) relative to the concentration of BCP in copaiba resin obtained from *Copaifera*. In some embodiments the copaiba resin is from *Copaifera officinalis*. In some embodiments the composition comprises (a) crolechinic acid, hardwickiic acid, kolavenic acid copalic acid, and, optionally, 7-alpha-acetoxyhardwickiic acid, and (b) optionally, beta-caryophyllene. In some embodiments, the ratio of 7-alpha-acetoxyhardwickiic acid (if present), crolechinic acid, hardwickiic acid, kolavenic acid and copalic acid, taken together, to the beta-caryophyllene, when beta-caryophyllene is present, is at least 1:1 by weight. In some embodiments, the composition is added to the beverage at concentration of at least 1.25 microgram composition per ml beverage. In some embodiments, the composition is added to the beverage at a concentration of at least 2.5 microgram composition per ml beverage. In some embodiments, the composition is added to the beverage at a concentration of at least 3.75 microgram composition per ml beverage. In some embodiments, the composition is added to the beverage at a concentration of at least 5.0 microgram composition per ml beverage. In some embodiments, the composition is added to the beverage at a concentration of not more than 5.0 microgram composition per ml beverage. In some embodiments, the composition is allowed to contact the beverage for at least two days, at least three days, at least four days, or at least five days. In some embodiments, the composition is added to the beverage prior to pasteurization. In some embodiments, the composition is added to the beverage after pasteurization. In some embodiments the beverage is acidic. In some embodiments the beverage is fruit juice. In some embodiments the fruit juice is apple juice. In some embodiments the fruit juice is grape juice. In some embodiments the fruit juice is peach juice. In some embodiments the fruit juice is watermelon juice. In some embodiments, the fruit juice is clear orange juice. In some embodiments, the composition is a composition as described above. In some embodiments, the composition has been prepared by a method as described hereinabove.

There is also provided, in accordance with an embodiment of the invention, a beverage in a container, the beverage containing a composition comprising (a) crolechinic acid, hardwickiic acid, kolavenic acid, copalic acid, and, optionally, 7-alpha-acetoxyhardwickiic acid, and (b) optionally, beta-caryophyllene, as described herein. In some embodiments, the beverage is a clear beverage. In some embodiments, the beverage has a turbidity of not more than 5 Nephelometric Turbidity Units (NTU), as measured in accordance with the United States Environmental Protection Agency Method no. 180.1, published August 1993. In some embodiments, the beverage has a turbidity of not more than 4 NTU. In some embodiments, the beverage has a turbidity of not more than 3 NTU. In some embodiments, the beverage has a turbidity of not more than 2 NTU. In some embodiments, the beverage has a turbidity of not more than 1 NTU. In some embodiments, the composition is present in the beverage at concentration of at least 1.25 microgram composition per ml beverage. In some embodiments, the composition is present in the beverage at a concentration of at least 2.5 microgram composition per ml beverage. In some embodiments, the composition is present in the beverage at a concentration of at least 3.75 microgram composition per ml beverage. In some embodiments, the composition is present in the beverage at a concentration of at least 5.0 microgram composition per ml beverage. In some embodiments, the composition is present in the beverage at a concentration of not more than 5.0 microgram composition per ml beverage. In some embodiments the beverage is acidic. In some embodiments the beverage is a fruit juice. In some embodiments the fruit juice is apple juice. In some embodiments the fruit juice is grape juice. In some embodiments the fruit juice is peach juice. In some embodiments the fruit juice is watermelon juice. In some embodiments the fruit juice is clear orange juice. In some embodiments, the composition is a composition as described above. In some embodiments, the composition has been prepared by a method as described hereinabove.

There is also provided, in accordance with an embodiment of the invention, a beverage in a container, the beverage containing a composition prepared by extracting *Copaifera* resin with a mixture of water and ethanol, and collecting the upper fraction obtained from the extraction to obtain the composition. In some embodiments, the beverage is a clear beverage. In some embodiments, the beverage has a turbidity of not more than 5 Nephelometric Turbidity Units (NTU), as measured in accordance with the United States Environmental Protection Agency Method no. 180.1, published August 1993. In some embodiments, the beverage has a turbidity of not more than 4 NTU. In some embodiments, the beverage has a turbidity of not more than 3 NTU. In some embodiments, the beverage has a turbidity of not more than 2 NTU. In some embodiments, the beverage has a turbidity of not more than 1 NTU. In some embodiments the composition comprises (a) crolechinic acid, hardwickiic acid, kolavenic acid, copalic acid, and, optionally, 7-alpha-acetoxyhardwickiic acid, and (b) optionally, beta-caryophyllene, as described herein. In some embodiments, the composition is present in the beverage at concentration of at least 1.25 microgram composition per ml beverage. In some embodiments, the composition is present in the beverage at a concentration of at least 2.5 microgram composition per ml beverage. In some embodiments, the composition is present in the beverage at a concentration of at least 3.75 microgram composition per ml beverage. In some embodiments, the composition is present in the beverage at a concentration of at least 5.0 microgram composition per ml beverage. In some embodiments, the composition is present in the beverage at a concentration of not more than 5.0 microgram composition per ml beverage. In some embodiments the beverage is acidic. In some embodiments the beverage is fruit juice. In some embodiments the fruit juice is apple juice. In some embodiments the fruit juice is grape juice. In some embodiments the fruit juice is peach juice. In some embodiments the fruit juice is watermelon juice. In some embodiments the fruit juice is clear orange juice. In some embodiments, the composition is a composition as described above. In some embodiments, the composition has been prepared by a method as described hereinabove.

There is also provided, in accordance with an embodiment of the invention, a method of controlling the growth of Gram-positive bacteria, including spores of Gram-positive bacteria, in a beverage, comprising adding to the beverage a composition comprising (a) crolechinic acid, hardwickiic acid, kolavenic acid, copalic acid, and, optionally, 7-alpha-acetoxyhardwickiic acid, and (b) optionally, beta-caryophyllene, as described herein. In some embodiments, the beverage is a clear beverage. In some embodiments, the beverage has a turbidity of not more than 5 Nephelometric Turbidity Units (NTU), as measured in accordance with the United States Environmental Protection Agency Method no. 180.1, published August 1993. In some embodiments, the beverage has a turbidity of not more than 4 NTU. In some embodiments, the beverage has a turbidity of not more than 3 NTU. In some embodiments, the beverage has a turbidity of not more than 2 NTU. In some embodiments, the beverage has a turbidity of not more than 1 NTU. In some embodiments, the composition is added to the beverage at concentration of at least 1.25 microgram composition per ml beverage. In some embodiments, the composition is added to the beverage at a concentration of at least 2.5 microgram composition per ml beverage. In some embodiments, the composition is added to the beverage at a concentration of at least 3.75 microgram composition per ml beverage. In some embodiments, the composition is added to the beverage at a concentration of at least 5.0 microgram composition per ml beverage. In some embodiments, the composition is added to the beverage at a concentration of not more than 5.0 microgram composition per ml beverage. In some embodiments, the composition is allowed to contact the beverage for at least two days, at least three days, at least four days, or at least five days. In some embodiments, the composition is added to the beverage prior to pasteurization. In some embodiments, the composition is added to the beverage after pasteurization. In some embodiments the beverage is acidic. In some embodiments the beverage is a fruit juice. In some embodiments the fruit juice is apple juice. In some embodiments the fruit juice is grape juice. In some embodiments the fruit juice is peach juice. In some embodiments the fruit juice is watermelon juice. In some embodiments the fruit juice is clear orange juice. In some embodiments the fruit juice is watermelon juice. In some embodiments, the composition is a composition as described above. In some embodiments, the composition has been prepared by a method as described hereinabove.

BRIEF DESCRIPTION OF THE DRAWINGS

Embodiments of the invention will be better understood in conjunction with the figures, in which.

DETAILED DISCUSSION

Figure 1A:
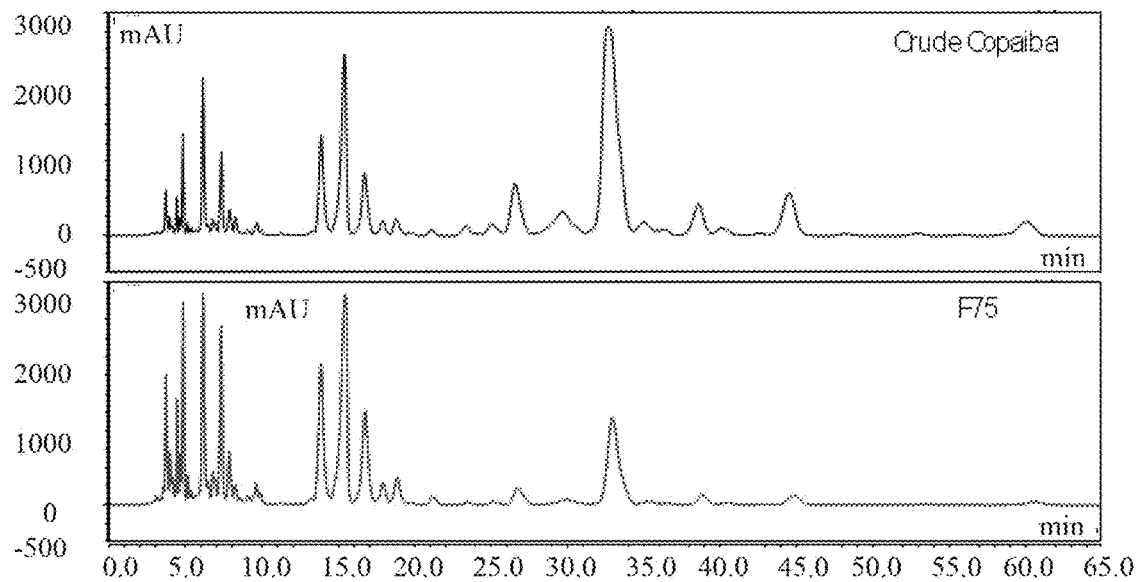
FIG. 1A shows HPLC elution profiles for crude copaiba resin and an upper extract obtained therefrom.

As noted, in accordance with an embodiment of the invention there is provided a method of preparing a composition which is active against spores of *Alicyclobacillus* and has a reduced concentration of beta-caryophyllene relative to copaiba resin obtained from *Copaifera*. The method comprises extracting resin obtained from *Copaifera* with a mixture of water and ethanol. Typically the mixture of ethanol and water will contain from 50% to 80% ethanol by weight, and from one to ten volumes of the mixture per volume of *Copaifera* resin will be used. An example of such an extraction is provided below. When the phases are allowed sufficient time to separate (usually about 20 minutes), two fractions result, an upper fraction and a lower fraction. The upper fraction, sometimes referred to herein as "Fraction 1", has been found to kill Gram-positive bacteria, including bacterial pathogens associated with food such as *Listeria monocytogenes, Bacillus cereus*, and Methicillin-resistant *Staphylococcus aureus*, as well as to kill bacteria in the form of spores.

Analysis of Fraction 1, detailed below, shows that it contains five different anti-bacterial diterpene compounds: 7-alpha-acetoxyhardwickiic acid, crolechinic acid, hardwickiic acid, kolavenic acid and copalic acid. This suggests that the possibility of any bacterium developing resistance against Fraction 1 is extremely low. Additionally, it was found that Fraction 1 is heat resistant, remaining active even after heat treatment of 121° C. for 15 minutes.

Because of this heat resistance, the presently recited compositions may be added to fruit juices and other clear beverages prior to pasteurization in order to avoid the outgrowth of spores that survive pasteurization, although addition after pasteurization is possible. Mixing of the composition in the beverage has been found aid in the efficacy of the composition, and it is expected that when used on an industrial scale, suitable mixing means will be employed, whether the composition is added to the beverage in a continuous manner, e.g. as the beverage is passed through a conduit, or whether the composition is added batch-wise. Often, when beverages are prepared on an industrial scale, a beverage concentrate is mixed in water, sometimes with additional ingredients, and thereafter pasteurized, A composition in accordance with embodiments of the present invention may be added to the beverage during this mixing phase, so that the composition is mixed into the beverage; for present purposes, addition of the composition at this stage constitutes addition of the composition to the beverage, and the resulting mixture constitutes beverage to which the composition has been added. It will also be appreciated that the composition may be added to a large quantity of beverage, e.g. to a vat containing several hundred or even thousands of liters of beverage, or it may be added to individual containers holding the beverage, e.g. to a bottle, carton or other package containing e.g. 2000, 1000, 500, 330, or 250 ml of beverage.

For present purposes, when reference is made to a clear beverage, it means the beverage (a) has a turbidity of not more than 3 Nephelometric Turbidity Units (NTU), as measured in accordance with the United States Environmental Protection Agency Method no. 180.1, published August 1993, the contents of which are incorporated herein by reference in their entirety. In addition to clear fruit juices such as clear apple juice, clear grape juice, clear peach juice, an clear watermelon juice, clear beverages include e.g. iced teas meeting the turbidity criterion, and sweetened drinks presently marketed in Israel as "fruit water". These drinks are generally acidic, and contain sugar, e.g. fructose, which can serve as a nutrient for the bacteria. Thus, an example of such a beverage has 94% water, fructose, flavorings, sodium citrate, and edible acids such as phosphoric acid and citric acid.

The following examples are illustrative of embodiments of the invention.

Example 1: Liquid-Liquid Extraction of Oil from *Copaifera officinalis*

Copaiba resins (also sometimes called copaiba oils) are produced by exudation from the trunks of trees belonging to the genus *Copaifera*. The resins have a characteristic odor of balsam and an aromatic, bitter, pungent taste. Pharmacological studies have demonstrated that copaiba resins have antimicrobial activity. The resins are composed mainly of sesquiterpenes, contributing their characteristic odor and taste and diterpenes that possess the antimicrobial activity. The sesquiterpene, beta-caryophyllene, is the most abundant molecule in Copaiba resins, making up approximately 40 percent by weight of the resins. The present examples used resin obtained from *Copaifera officinalis* grown in northern Brazil, in the states of Acre (AC), Amazonas (AM), Para (PA) and Rondonia (RO).

A mixture of 75% ethanol in water was mixed with crude copaiba resin obtained from *Copaifera officinalis*, in a ratio of 5:1 ethanol/water to copaiba resin w/w, for 20 minutes. The resultant mixture was allowed to stand until two distinct phases formed; usually a period of two to twelve hours was sufficient. The lower phase had a yellow color similar to the crude copaiba oil, and the upper phase (referred to hereinafter "Fraction 1") was clear and colorless. As will be explained below, relative to the crude resin, Fraction 1 is enriched for diterpenes and contains relatively low amounts of sesquiterpenes. Removal of the ethanol and water from Fraction 1 indicated that about 250 mg of material were recovered for each gram of crude resin used.

Similar results were obtained with a scaled-up procedure: 1000 g of the *Copaifera officinalis* resin was extracted using 5 liters of 75% ethanol in water, by mixing the liquids for 30 minutes and then allowing them to settle for several hours to achieve phase separation. Removal of the solvents from the upper phase yielded 25 g of material.

Similar results wore obtained with copaiba resin obtained from other *Copaifera* sources.

Example 2

Samples of the crude copaiba resin, Fraction 1, and the lower fraction (10 mg/ml) were each subjected to reverse-phase High Performance Liquid Chromatography (RP-HPLC) using a Dionex UltiMate 3000 system (Thermo Scientific) and a Phenomenex C-18 (4.6×250 mm) Luna column. Sample wore dissolved in 90% acetonitrile in water with 1% phosphoric acid and injected at a flow rate of 1 ml/min. The temperature of the column was 22° C., and detection was carried out at 210 nm. The final conditions used for analytic HPLC were as follows:

| Time | % of 90% acetonitrile in water with 1% phosphoric acid | % Water |
|---|---|---|
| 0 | 100 | 0 |
| 20 min | 90 | 10 |
| 70 min | 90 | 10 |

Figure 1B:
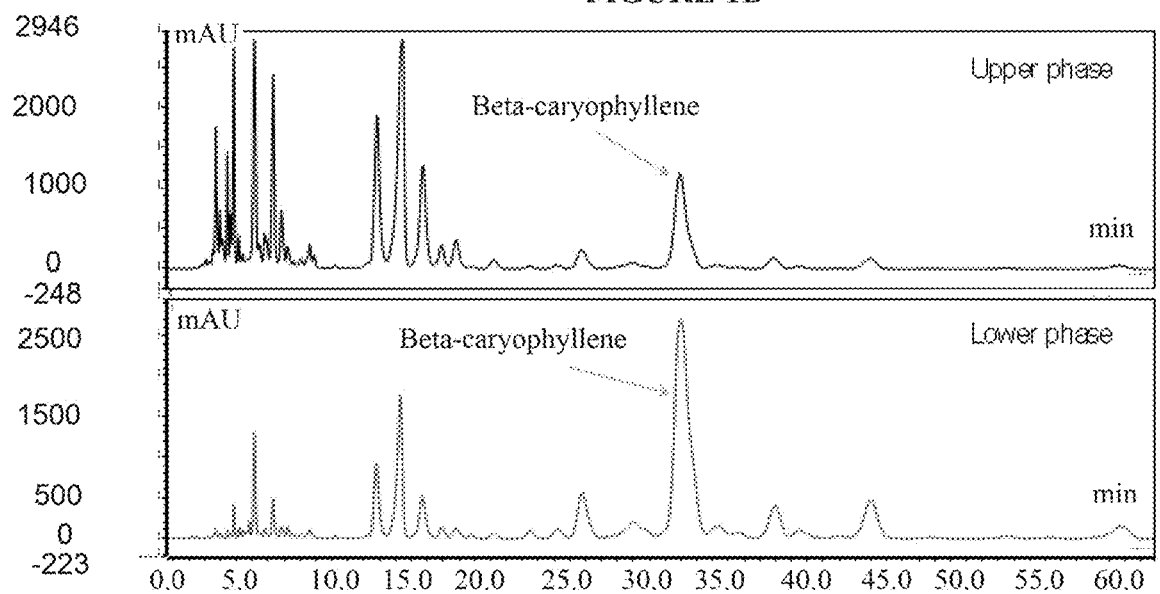
FIG. 1B shows HPLC elution profiles for the upper and lower extracts obtained therefrom.

The results, presented in FIG. 1, showed that, relative to the crude resin and relative to the lower fraction, Fraction 1 was enriched in materials eluting in the first 20 minutes, and poorer in materials eluting thereafter. In this and all other figures showing elution profiles, the numbers along the axes denote time in minutes.

Figure 2:
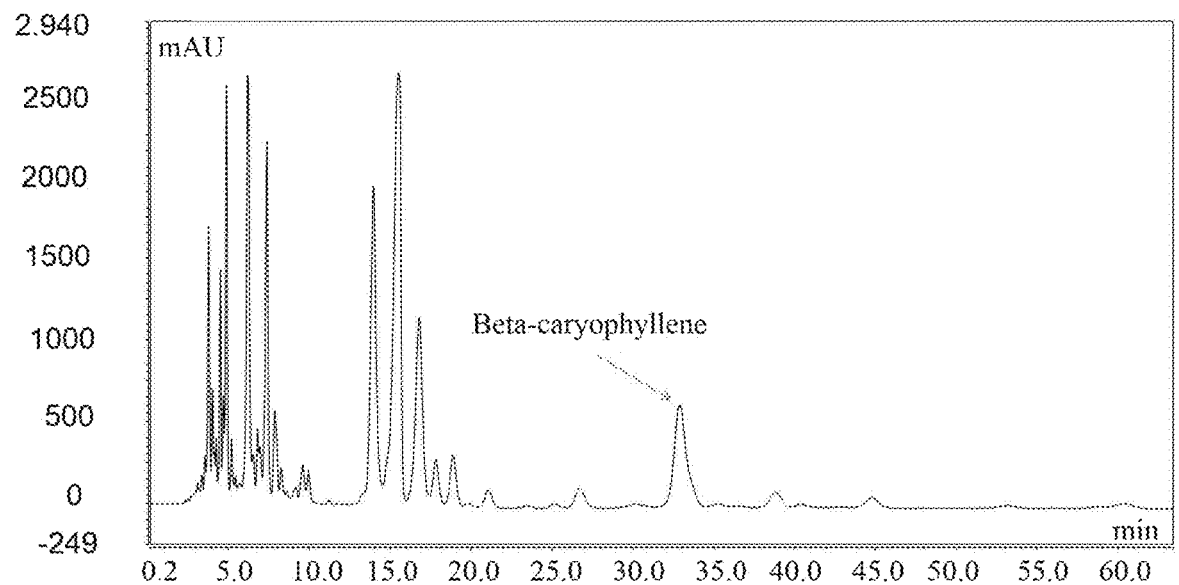
FIG. 2 shows an HPLC elution profile for an extract obtained from copaiba resin.

The elution profile for the material obtained in the scaled-up extraction described above was substantially the same, as shown in FIG. 2.

Figure 16:
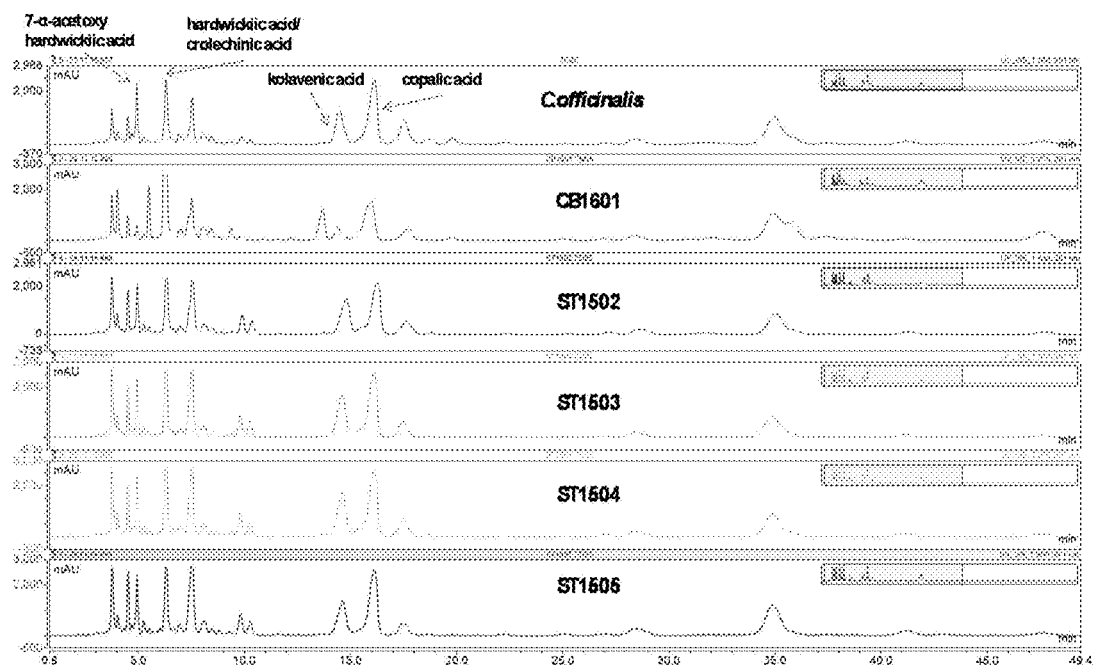
FIG. 16 shows HPLC elution profiles for upper extracts obtained from different sources of crude copaiba resin.

FIG. 16 show's the HPLC elution profile for upper phases obtained under the same extraction conditions and HPLC conditions as used for *Copaifera officinalis*, following extracted from resin from other *Copaifera* species.

Example 3: pH Effects

Figure 3:
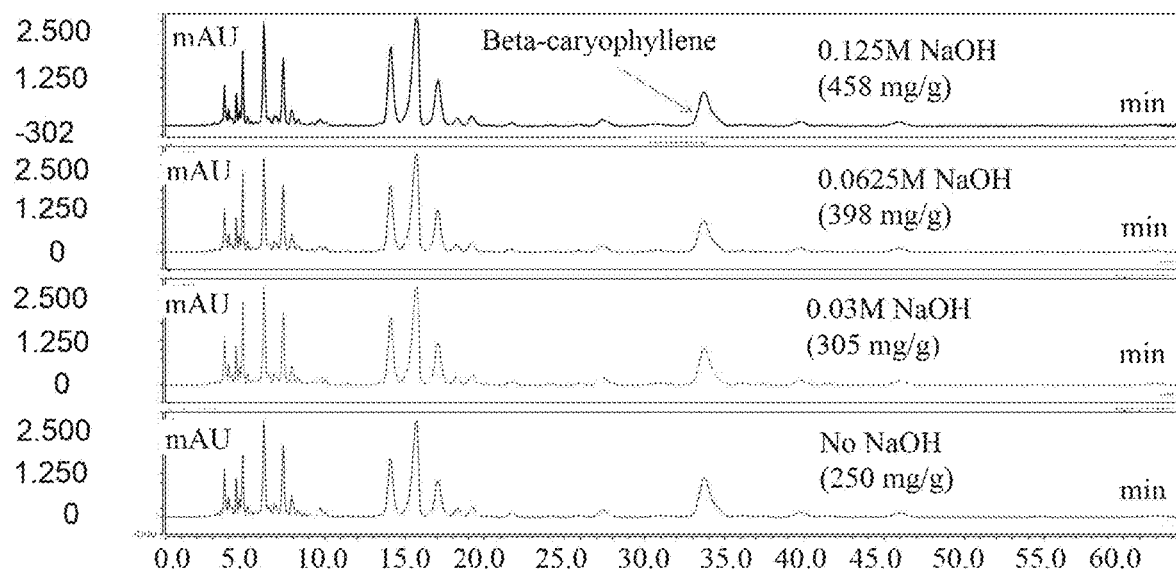
FIG. 3 shows HPLC elution profiles for extract obtained from copaiba resin at increasing pH values.

It was found that increasing the pH of the extraction mixture by addition of NaOH, up to a concentration of 0.125 molar NaOH, increased the yield of Fraction 1, while maintaining a similar RP-HPLC elution profile under the conditions described in Example 2, as shown in FIG. 3.

Figure 4:
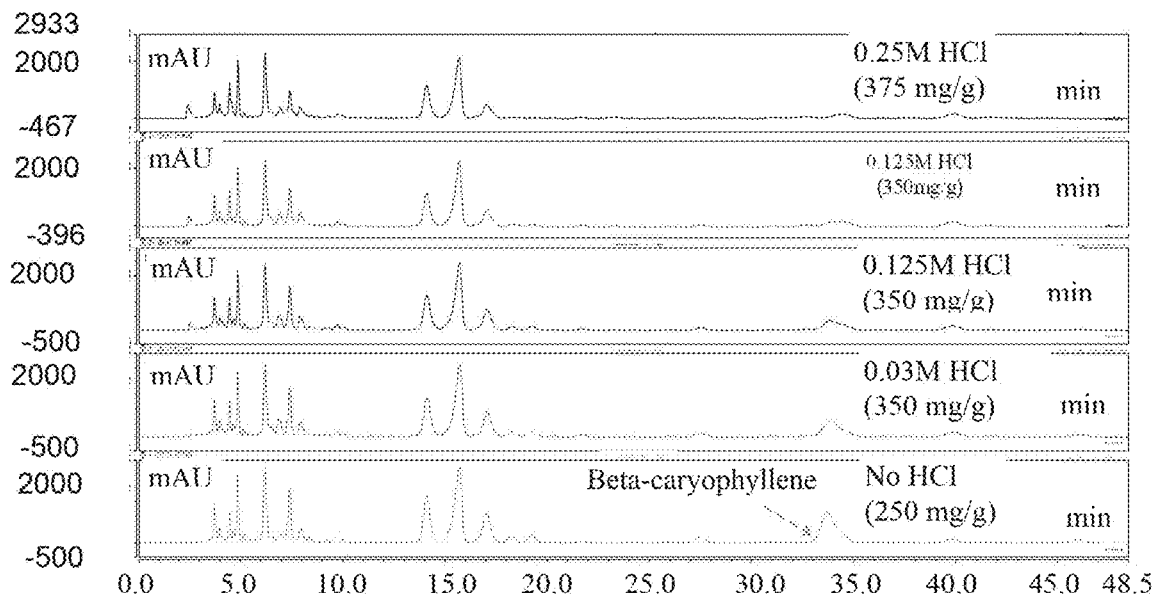
FIG. 4 shows HPLC elution profiles for extract obtained from copaiba resin at decreasing pH values.

Decrease of pH of the extraction mixture by addition of HCl, up to a concentration of 0.25 molar HCl, also increased the yield of Fraction 1, and significantly decreased the presence of beta-caryophyllene therein, as shown in the RP-HPLC elution profile obtained under the conditions described in Example 2, shown in FIG. 4.

Example 4: Identification of Principal Components of Fraction 1

Figure 5:
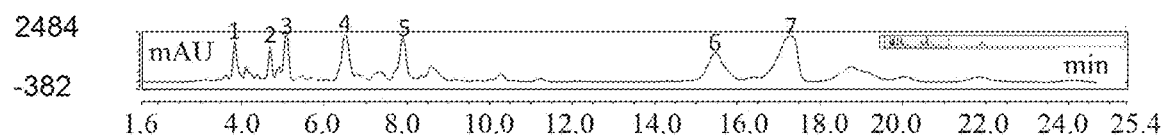
FIG. 5 shows an HPLC elution profile for an extract obtained from copaiba resin, with the seven principal peaks labeled 1-7.

The seven principal components of Fraction 1 (see FIG. 5) were identified as follows:

First, a quantity of each component was collected from Fraction 1 by semi-preparative RP-HPLC, using a Dionex UltiMate 3000 system and a Phenomenex C-18 (10×250 mm) Luna column. Each sample was dissolved in 90% acetonitrile in water with 0.05% formic acid and injected at a flow rate of 5 ml/min. The temperature of the column was 22° C., and detection was earned out at 210 nm. The final conditions used for semi-preparative HPLC were as follows:

| Time | % of 90% acetonitrile in water with 0.05% formic acid | % Water |
|---|---|---|
| 0 | 100 | 0 |
| 20 min | 90 | 10 |
| 70 min | 90 | 10 |

Figure 6:
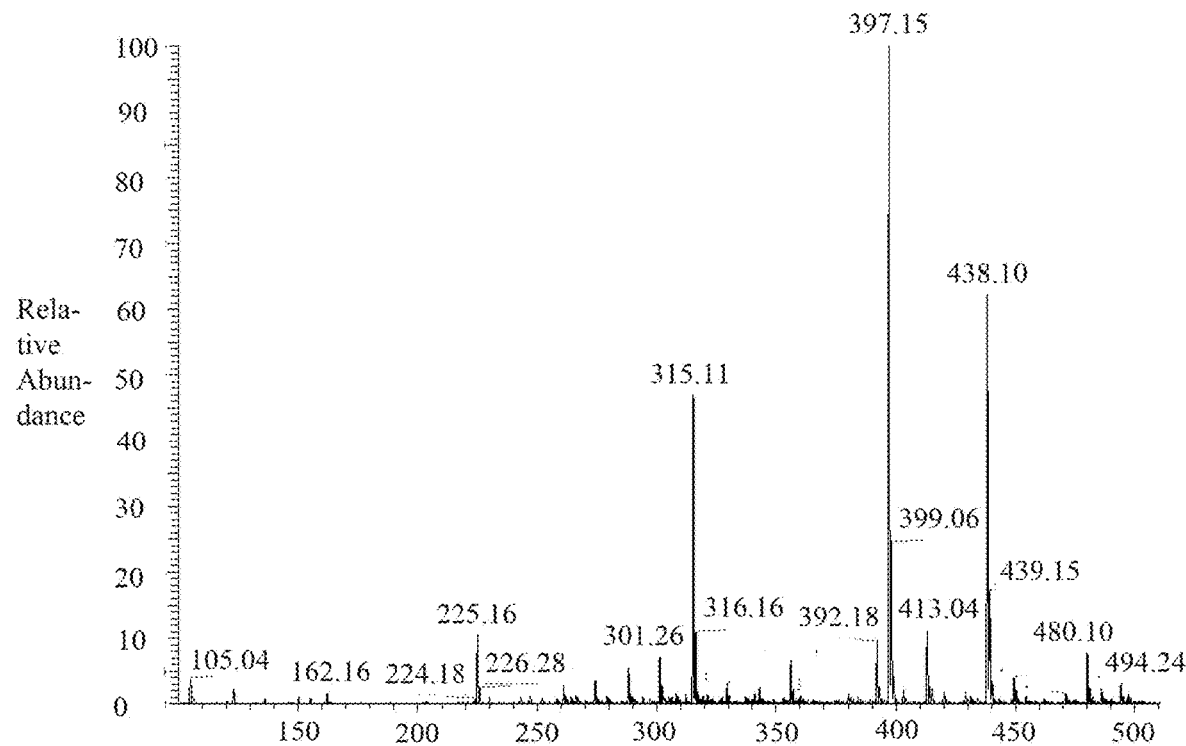
FIG. 6 shows a mass spectrograph for the material corresponding to peak 3 in FIG. 5.

Each collected fraction was then purified by RP-HPLC as described in Example 2. The seven fractions were tested for activity against spores of *Alicyclobacillus acidoterrestris*, as described below. The compounds in the four most active of these fractions were then identified using mass spectrometry and nuclear magnetic resonance (NMR), as follows:

Peak 3: The isolated compound was subjected to mass spectrometry (MS), which showed a major component with a mass-to-charge ratio (m/z) of 397.15 [M+Na]$^+$ (see FIG. 6), According to the accurate mass, 374.22 g/mol, the molecular formula was predicted as $C_{22}H_{30}O_6$.

Figure 7:
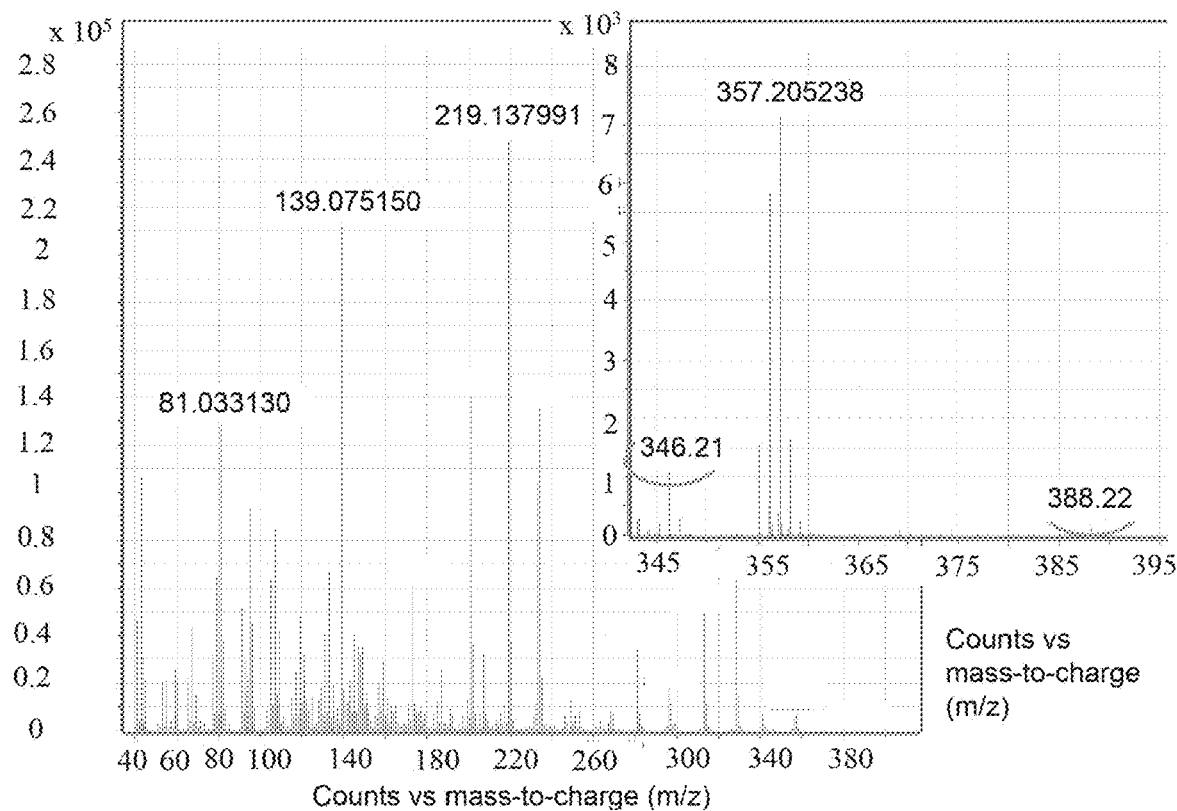
FIG. 7 shows a mass spectrograph for material corresponding to peak 3 in FIG. 5, following methylation.

After methylation of the compound with trimethylsilyl-diazomethane (TMS-diazomethane, procedure described by Hashimoto et al., *Chem. Pharm. Bull.* 1981, 29, 1475-1478), the methylated compound was subjected to gas chromatography-MS (GC-MS). The analysis of the MS/MS fragmentation pattern showed a minor peak with m/z 388.22 (corresponding to the methylated molecule) and a daughter peak with m/z 346.21 (see FIG. 7).

Analysis of the $^1$H-$^{13}$C and two-dimensional nuclear magnetic resonance spectroscopy (2D-NMR) of the free acid (see the table below, which presents results of $^{13}$C-NMR) resulted in the determination of the molecule's structure. The isolated compound was found to be 7-α-acetoxy-hardwickiic acid.

| Position | $^{13}$C NMR $\delta_c$ (ppm) | J |
|---|---|---|
| 1 | 17.3 | |
| 2 | 27.45 | |
| 3 | 140.15 | 6.88 d |
| 4 | 141.46 | |
| 5 | 36.97 | |
| 6 | 38.26 | |
| 7 | 74.75 | 5.23 |
| 8 | 38.49 | |
| 9 | 39.27 | |
| 10 | 46.53 | |
| 11 | 39.63 | |
| 12 | 18.52 | |
| 13 | 125.29 | |
| 14 | 111.06 | 6.28 s |
| 15 | 143.00 | 7.23 s |
| 16 | 138.59 | 7.38 s |
| 17 | 12.17 | 0.96 s |
| 18 | 21.63 | |
| 19 | 170.72 | 1.47 s |
| 20 | 19.73 | 1.05 s |
| CO$_2$Me | 169.83 | |
| MeCO$_2$ | 22.27 | 2.1 s |
| Solvent (CDCl$_3$) | 77.16 | |

Figure 8:
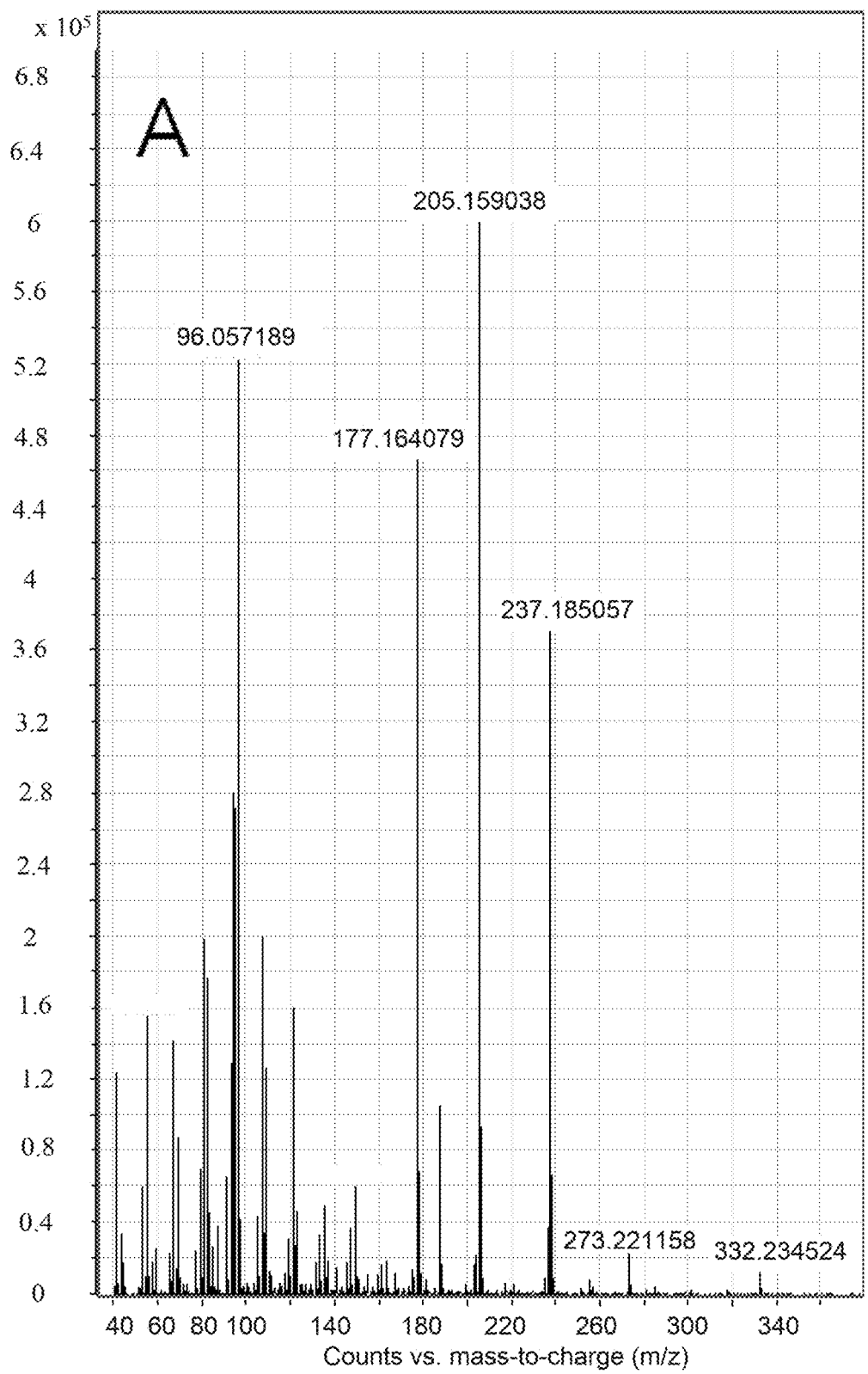
FIG. 8 shows a mass spectrograph for some material corresponding to peak 4 in FIG. 5, following methylation.
Figure 9:
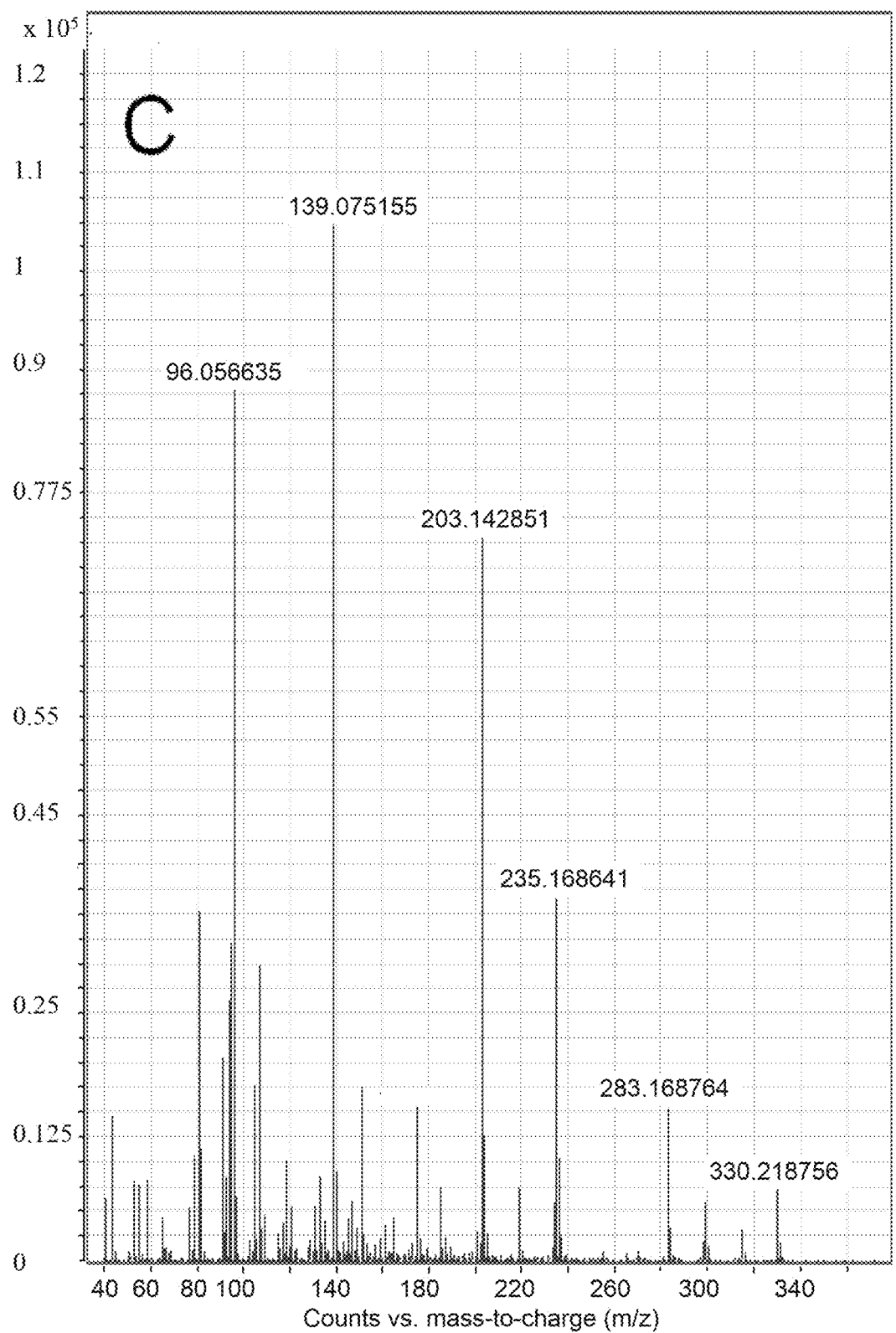
FIG. 9 shows a mass spectrograph for some material corresponding to peak 4 in FIG. 5, following methylation.

The material in this fraction was methylated with TMS-diazomethane. GC-MS analysis (conditions recited below, applicable to this and the other examples herein) of the methylated material showed that this isolated HPLC peak in fact contains two compounds. The first peak in the GC-MS chromatogram (retention time 26.9 min) had the following fragmentation pattern: m/z 332, 273, 237, 205, 177, 96 (See FIG. 8), this fragmentation pattern is consistent with the methyl ester of crolechinic acid. The second peak was detected at 27.1 min and showed the following fragmentation pattern: m/z 330, 283, 235, 203, 139, 96 (see FIG. 9). By comparison to the spectra in the National Institute of Standards and Technology database, this compound was identified as methyl hardwickiate, the methyl ester of hardwickiic acid. Additionally, according to the accurate masses of the two corresponding methyl esters, 332.2346 g/mol and 330.2189 g/mol, the predicted molecular formulas of the methylated compounds were respectively $C_{21}H_{32}O_3$ and $C_{21}H_{30}O_3$. The predicted structures for the free acids were confirmed by $^1$H, $^{13}$C and 2D-NMR, see table immediately following which provides data for a mixture of crolechinic acid and hardwickiic acid in approximately a 3:7 molar ratio.

| Position | $^{13}$C NMR $\delta_c$ (ppm) | $^1$H NMR $\delta_H$ (ppm) |
|---|---|---|
| 1 | 17.6 | 1.30-182 |
| 2 | 27.64 | 2.12-2.27 2.27-2.37 |
| 3 | 140.31 | 6.85 |
| 4 | 141.36 | |
| 5 | 37.75 | |
| 6 | 35.96 | 2.43, 1.17 |
| 7 | 27.42 | 130-1.82 |
| 8 | 36.40 | 1.30-1.82 |
| 9 | 38.96 | |

| Position | $^{13}$C NMR $\delta_c$ (ppm) | $^1$H NMR $\delta_H$ (ppm) |
|---|---|---|
| 10 | 46.82 | 1.30-1.82 |
| 11 | 38.76 | 1.30-1.82 |
| 12 | 18.33 | 2.12-2.27 |
|  |  | 2.27-2.37 |
| 13 | 125.73 |  |
| 14 | 111.14 | 6.26 |
| 15 | 142.88 | 7.35 |
| 16 | 138.54 | 7.20 |
| 17 | 16.18 | 0.84 |
| 18 | 170.80 |  |
| 19 | 20.6 | 1.26 |
| 20 | 18.44 | 0.76 |
| Solvent (CDCl$_3$) | 77.16 | 7.26 |

Thus the isolated fraction pertaining to peak 4 contains a mix of crolechinic acid and hardwickiic acid in a ratio of approximately 1:2 respectively.

Gas chromatograph: Agilent GC 7890B, sample inlet GC (injection source PAL sampler, injection size 1 microliter), oven temperature initial 50° C., hold time 3 min, raised 10° C./minute to 280° C., hold time 10 min, raised 20° C./min to 300° C., hold time 7 min, SS inlet mode split, carrier gas helium, heater 250° C., split ratio 10:1, split flow 10 ml/min, transfer line temp 280° C., Agilent DB-5 ms DuraGuard 30 m×250 micrometer×0.25 micrometer (+10 m guard), flow 1 ml/min.

Mass spectrometry: Agilent 7200 Q-TOF spectrometer, ionization mode EI, source temperature 230° C., EI energy 70 eV, quadrupole temp 150° C., solvent delay 5 min, mass range 40-700 amu, acquisition rate 5 spectra/second, threshold 100 counts.

Figure 10:
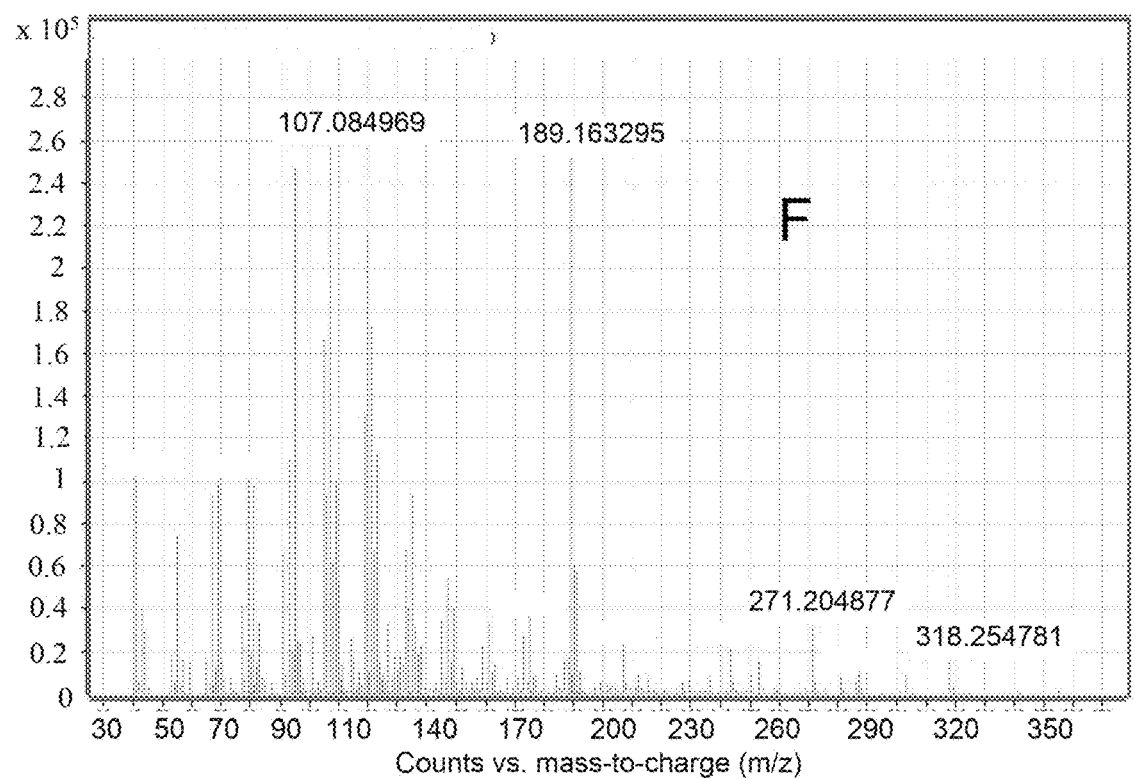
FIG. 10 shows a mass spectrograph for material corresponding to peak 6 in FIG. 5, following methylation.

Peak 6:

The fraction corresponding to peak 6 was methylated using TMS-diazomethane. GC-MS analysis of the methylated compound yielded an MS fragmentation pattern showing a molecular ion at m/z 318 corresponding to the formula $C_{21}H_{34}O_2$ (see FIG. 10). Analysis of $^1$H-$^{13}$C and 2D-NMR spectra (see table below) of the unmethylated compound, and comparison with values reported in the literature (Pacheco, Molecules 2009, 14(3), pp, 1245-1262, Salah, J, Agr. & Food Chem. 2003, 51(26), pp. 7607-7610) indicated that the isolated compound was Kolavenic acid.

| Position | $^1$H NMR $\delta_H$ (ppm) | $^{13}$C NMR $\delta_c$ (ppm) | $^{13}$C NMR $\delta_c$ (ppm), Ref (2) | $^{13}$C NMR $\delta_c$ (ppm), Ref (3) |
|---|---|---|---|---|
| Solvent | CDCl$_3$ | CDCl$_3$ | CDCl$_3$ | CDCl$_3$ |
| 1 |  | 18.45 | 17.3 | 18.7 |
| 2 |  | 27.59 | 27.5 | 27.3 |
| 3 | 5.19 (t) | 120.55 | 120.5 | 120.8 |
| 4 |  | 144.61 | 144.5 | 144.8 |
| 5 |  | 38.91 | 38.3 | 38.6 |
| 6 |  | 36.4 | 36.4 | 37.2 |
| 7 |  | 27.02 | 26.9 | 27.8 |
| 8 |  | 36.4 | 36.4 | 36.7 |
| 9 |  | 38.33 | 38.4 | 39.2 |
| 10 |  | 46.62 | 46.6 | 46.9 |
| 11 |  | 35.03 | 35.0 | 35.3 |
| 12 |  | 36.91 | 36.9 | 36.7 |
| 13 |  | / | 164.4 | 164.9 |
| 14 | 5.7 (s) | / | 114.9 | 115.1 |
| 15 |  | / | 172.0 | 171.9 |
| 16 | 2.17 (s) | 19.57 | 19.5 | 19.8 |
| 17 | 0.81 (d) | 16.1 | 15.9 | 16.3 |
| 18 | 1.59 (s) | 18.14 | 18.3 | 18.3 |
| 19 | 1.00 (s) | 20.08 | 20.0 | 20.3 |
| 20 | 0.73 (s) | 18.43 | 17.9 | 18.6 |

Figure 11:
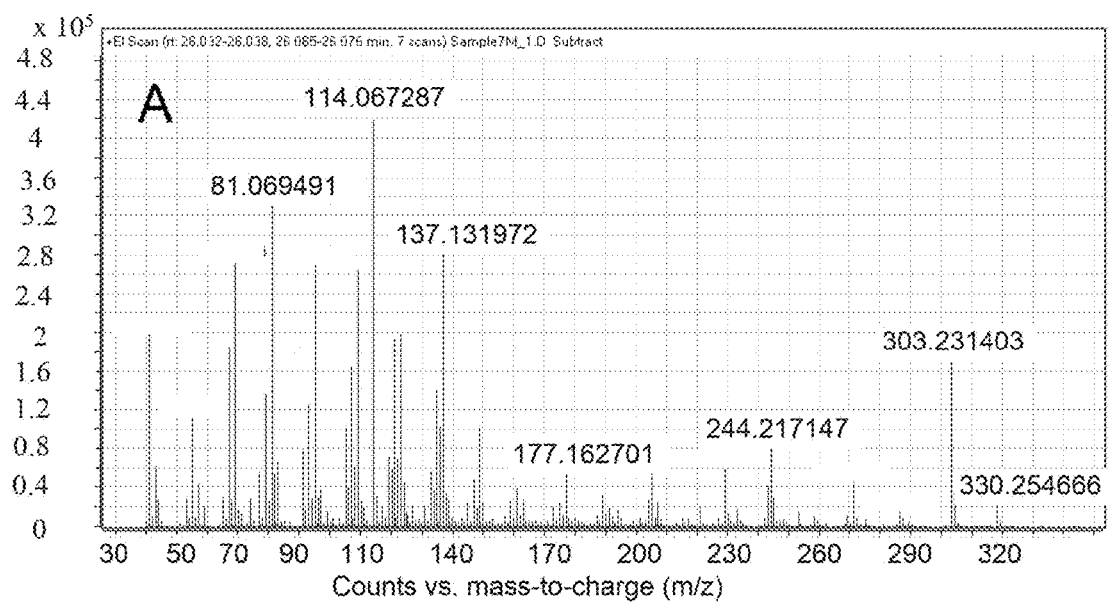
FIG. 11 shows a mass spectrograph for material corresponding to peak 7 in FIG. 5, following methylation.
Figure 12:
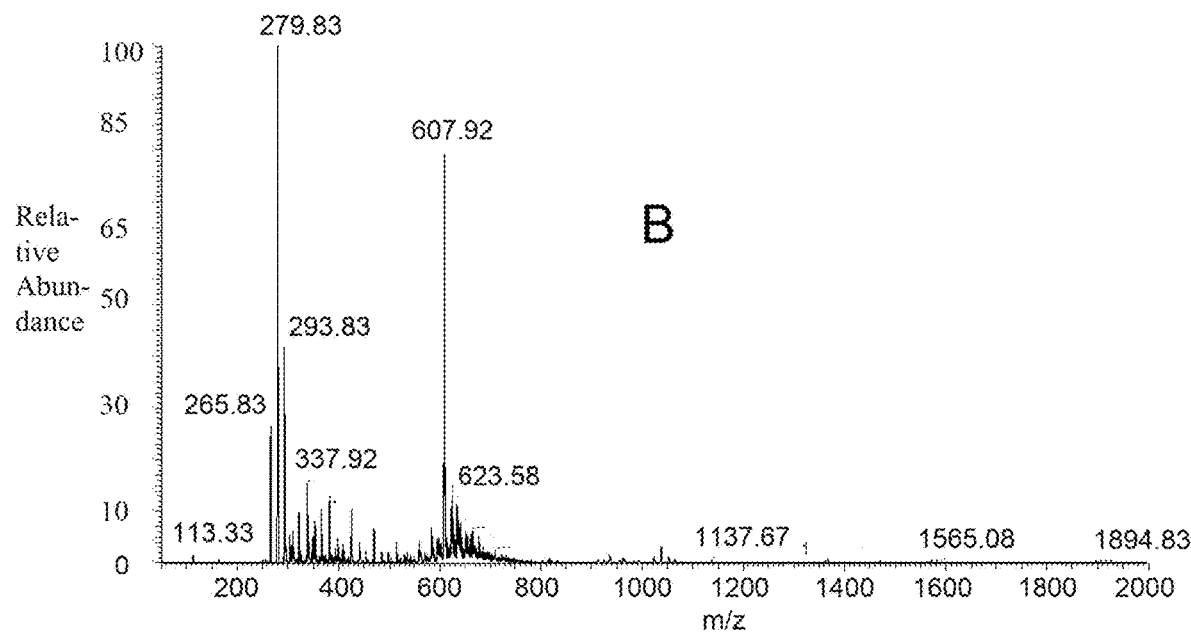
FIG. 12 shows a mass spectrograph for material corresponding to peak 7 in FIG. 5, following methylation.

Peak 7:

The fraction corresponding to peak 7 was methylated using TMS-diazomethane. GC-MS analysis of the methylated compound yielded an MS fragmentation pattern showing a molecular ion at m/z 318.25 (see FIG. 11) suggesting the molecular formula $C_{21}H_{34}O_2$. By comparison of the fragmentation pattern with NIST data, it was determined to correspond to methyl copalate, the methyl ester of copalic acid. This result was confirmed by liquid chromatography-mass spectrometry (LC-MS). The fragmentation pattern showed a major peak with a m/z 607 corresponding to the deprotonated dimer of copalic acid (see FIG. 12).

Example 5: Comparison of Relative Amounts of Components in Raw Copaiba Resin and Fraction 1

Using analytical RP-HPLC as described above, and using the Chromeleon 7.0 software (Thermo Fisher Scientific) to calculate areas under the curve for the peaks, the following relative amounts of each of the five acids listed above and beta-caryophyllene were found, although it will be appreciated that these numbers provide only an approximation for the relative amounts of these six components:

| Compound | % of Crude copaiba oleoresin | % of Fraction 1 |
|---|---|---|
| 7-α-acetoxyhardwickiic acid | 1.02 | 3.65 |
| Hardwickiic acid + crolechinic acid | 2.79 | 6.03 |
| Kolavenic acid | 4.14 | 6.89 |
| copalic acid | 9.07 | 15.51 |
| beta caryophyllene | 33.94 | 12.58 |

It will be appreciated that in view of the present disclosure, RP-HPLC can be used to determine the suitability of a given sample of *Copaifera* resin for extraction to obtain a composition as described herein.

Example 6: Testing of Fractions Collected in Example 4

The fractions collected in Example 4, as well as Fraction 1 and nisin, a preservative presently in common use in the industry, were tested for activity by incubating for the times indicated in the table below with *Alicyclobacillus acidoterrestris* (JCM catalogue number 21547, IAM Culture Collection no. 15086) in apple juice. The minimum inhibitory concentration (MIC) was determined by optical density measurements at 600 nm, and by counting colony forming units (CFU) as follows: after four days of incubation at 37° C., juice samples were serially diluted in 10-fold increments (10-fold, 100-fold, 1000-fold, etc.) and plated on Potato Dextrose Agar (PDA). Plates were incubated at 45° C. for at least 48 hours, and colonies were counted to determine CFU/ml. The MIC found is indicated in the table.

| Sample | MIC (µg/ml) in 100% apple juice 2 days of incubation | MIC (µg/ml) in 100% apple juice 3 days of incubation | MIC (µg/ml) in 100% apple juice 5 days of incubation | MIC (µg/ml) in 100% apple juice 7 days of incubation |
|---|---|---|---|---|
| Fraction 1 | 1.25 | 1.25 | 1.25 | 1.25 |
| 1 | 5 | 5 | 5 | 5 |
| 2 | No activity | No activity | No activity | No activity |
| 3 | 2.5 | 5 | 5 | 5 |
| 4 | 1.25 | 1.25 | 1.25 | 1.25 |
| 5 | 5 | 5 | 5 | 5 |
| 6 | 1.25 | 1.25 | 1.25 | 1.25 |
| 7 | 1.25 | 1.25 | 1.25 | 1.25 |
| Nisin | 10 | 10 | No activity | No activity |

Example 7

Figure 13:
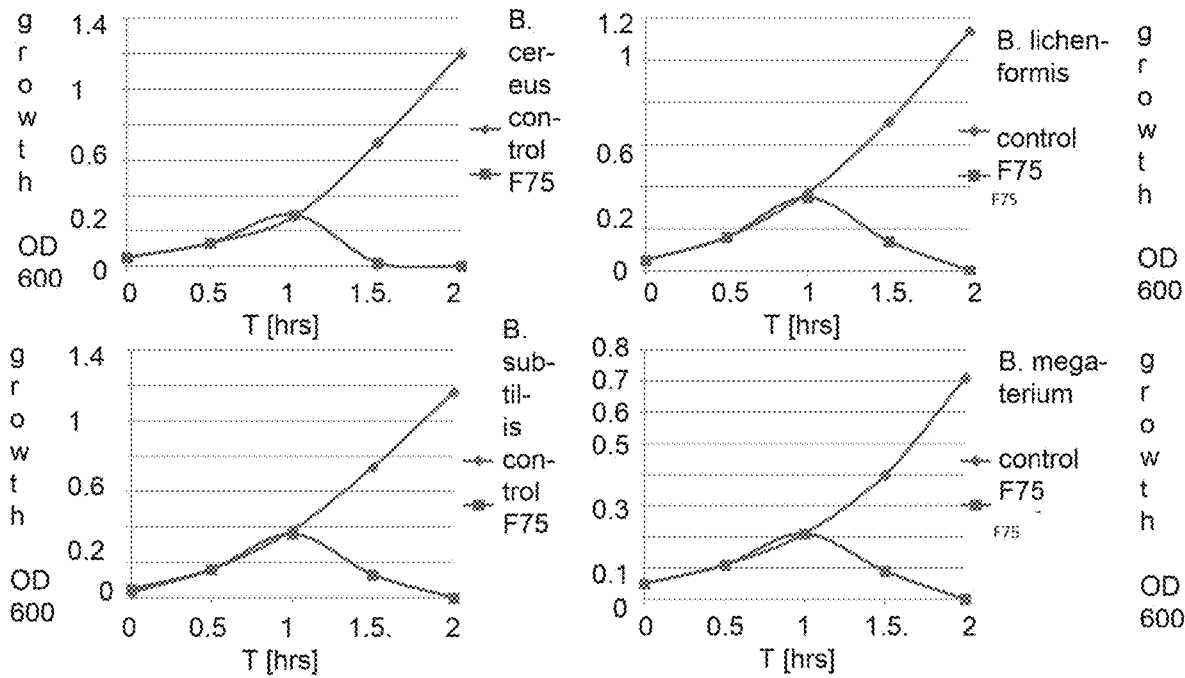
FIG. 13 shows the effect of fraction 1 on the growth of four spore-forming bacterial strains as measured by optical density at 600 nm.

Fraction 1 was tested against four spore-forming bacterial strains: *Bacillus cereus, Bacillus lichenformis, Bacillus megaterium* and *Bacillus subtilis* (PY79). Spores of these strains ($10^4$ spores/ml) were triggered to revive by inoculating them in Luria-Bertani (LB) broth at 37° C. After one hour, fraction 1 was added in a concentration of 5 µg fraction 1 per ml of broth. Absorbance at optical density of 600 nm (OD600) represents growth. It can be seen in FIG. 13 that in comparison to the untreated spores (control), treated spores were killed by Fraction 1 as indicated by decreasing OD600.

Example 8

Figure 14:
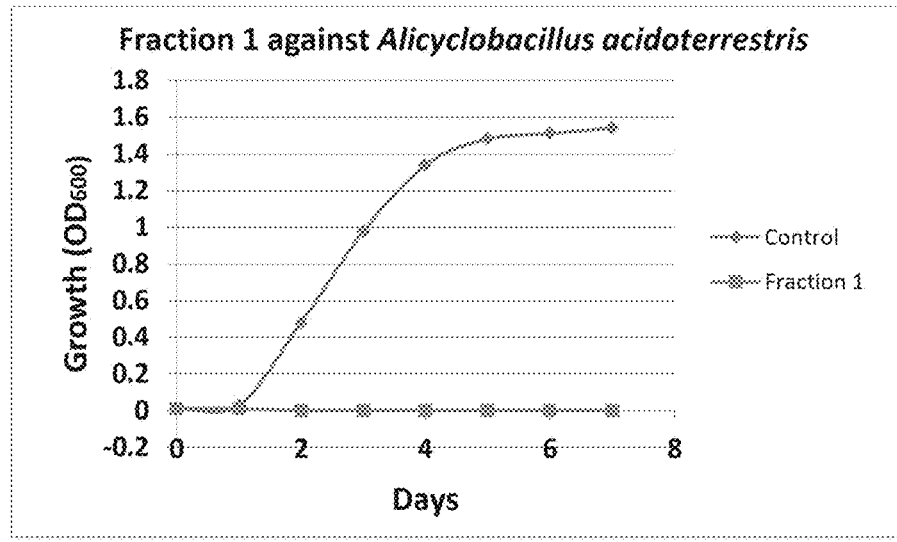
FIG. 14 shows the effect of fraction 1 on *Alicyclobacillus acidoterrestris* spores in commercial apple juice as measured by optical density at 600 nm.

Fraction 1 was tested against *Alicyclobacillus acidoterrestris* spores (JCM 21547) in commercial apple juice. The juice was supplemented with Fraction 1 at a concentration of 5 µg/ml, contaminated by adding $10^4$ of spores/ml and incubated at 37° C. Fraction 1 blocked *Alicyclobacillus acidoterrestris* spore outgrowth as indicated by measuring OD600 over seven days, see FIG. 14.

In comparison, the crude copaiba resin from which Fraction 1 was derived achieved a similar level of activity only at a concentration of 20 microgram/ml.

The fractions shown in FIG. 16 were similarly tested and all found to have activity against *Alicyclobacillus acidoterrestris*.

Fraction 1 was also tested for activity against *Alicyclobacillus acidoterrestris* in other clear beverages and found to be active.

Example 9

Figure 15:
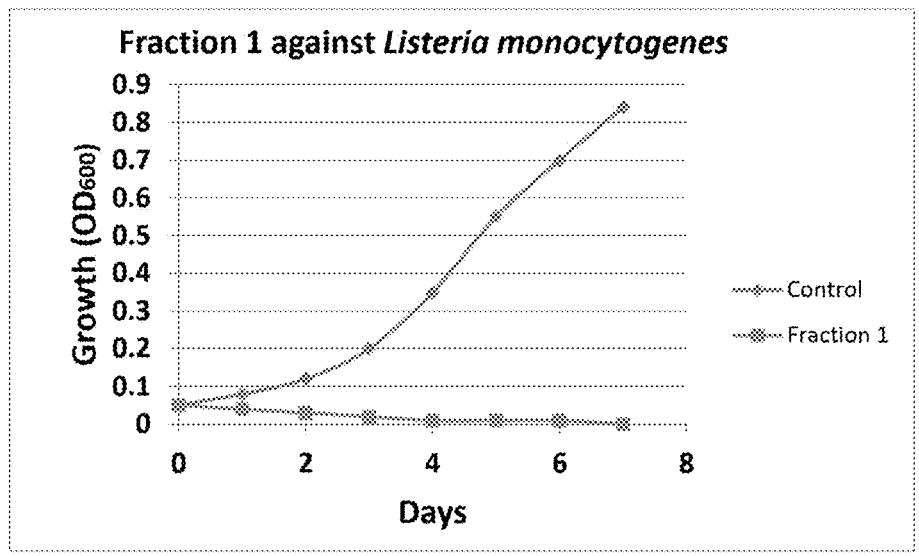
FIG. 15 shows the effect of fraction 1 on *Listeria monocytogenes* strain DP-L861 in Brain Heart Infusion medium as measured by optical density at 600 nm.

Fraction 1 was tested against *Listeria monocytogenes* strain DP-L861 in Brain Heart Infusion medium at 4° C. Culture was diluted to OD600 of 0.05, treated with Fraction 1 at a concentration of 15 µg/ml, and incubated at 4° C. for 7 days. Fraction 1 blocked *Listeria monocytogenes* growth at refrigeration temperature, as determined by OD600 measurements, see FIG. 15.

There is thus provided, in accordance with inventive concept 1, a composition of matter comprising (a) crolechinic acid, hardwickiic acid, kolavenic acid, copalic acid, and, optionally, 7-alpha-acetoxyhardwickiic acid, and (b) optionally, beta-caryophyllene (BCP), the ratio of said crolechinic acid, hardwickiic acid, kolavenic acid, copalic acid, and 7-alpha-acetoxyhardwickiic acid if present, taken together, to said beta-caryophyllene, when beta-caryophyllene is present, being at least 1:1 by weight.

Inventive concept 2. The composition of inventive concept 1 which comprises 7-alpha-acetoxyhardwickiic acid.

Inventive concept 3. The composition of inventive concept 1 or 2 which is substantially free of BCP.

Inventive concept 4. The composition of any one of inventive concepts 1 to 3, wherein the ratio of the crolechinic acid, hardwickiic acid, kolavenic acid, copalic acid, and 7-alpha-acetoxyhardwickiic acid, if present, taken together, to the beta-caryophyllene is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7, at least 2.8, at least 2.9:1, or at least 3.0:1 by weight.

Inventive concept 5. The composition of any one of inventive concepts 1 to 4, wherein the ratio of the crolechinic acid, hardwickiic acid, kolavenic acid, copalic acid, and 7-alpha-acetoxyhardwickiic acid, if present, taken together, to the beta-caryophyllene is not greater than 100:1 by weight.

Inventive concept 6. The composition of inventive concept 5, wherein the ratio of said crolechinic acid, hardwickiic acid, kolavenic acid, copalic acid and 7-alpha-acetoxyhardwickiic acid, if present, taken together, to said beta-caryophyllene is not greater than 90:1, not greater than 80:1, not greater than 70:1, not greater than 60:1, not greater than 50:1, not greater than 40:1 not greater than 30:1, not greater than 20:1, not greater than 10:1, not greater than 9:1, not greater than 8:1, not greater than 7:1, not greater than 6:1, not greater than 5:1, not greater than 4:1, or not greater than 3:1 by weight.

Inventive concept 7. The composition of any one of inventive concepts 1 to 6, wherein 7-alpha-acetoxyhardwickiic acid constitutes at least 7 wt. % of the amount of 7-alpha-acetoxyhardwickiic acid, crolechinic acid, hardwickiic acid, kolavenic acid and copalic acid taken together.

Inventive concept 8. The composition of inventive concept 7, wherein 7-alpha-acetoxyhardwickiic acid constitutes at least 10 wt. % of the amount of 7-alpha-acetoxyhardwickiic acid, crolechinic acid, hardwickiic acid, kolavenic acid and copalic acid taken together.

Inventive concept 9. The composition of any one of inventive concepts 1 to 8, wherein the composition is active against spores of *Alicyclobacillus*.

Inventive concept 10. The composition of any one of inventive concepts 1 to 9 wherein the composition is substantially free of hexane and dichloromethane.

There is also provided, in accordance with an inventive concept 11, a method of preparing a composition of any one of inventive concepts 1 to 10, which composition has, relative to the concentration of 7-alpha-acetoxyhardwickiic acid, crolechinic acid, hardwickiic acid, kolavenic acid and copalic acid taken together in copaiba resin obtained from *Copaifera*, a reduced concentration of beta-caryophyllene (BCP), the method comprising extracting resin obtained from *Copaifera* with a mixture of water and ethanol, and collecting the upper fraction obtained from the extraction, whereby to obtain the composition.

Inventive concept 12. The method of inventive concept 11, wherein the composition is active against spores of *Alicyclobacillus*.

Inventive concept 13. The method of inventive concept 11 or 12, wherein the copaiba resin is obtained from *Copaifera officinalis*.

Inventive concept 14. The method of any one of inventive concepts 11 to 13, wherein the composition is active against spores of *Alicyclobacillus acidoterrestris*.

Inventive concept 15. The method of any one of inventive concepts 11 to 14, wherein the ratio of ethanol to water in the mixture is at least 1:1 by weight.

Inventive concept 16. The method of inventive concept 15, wherein the ratio of ethanol to water in the mixture is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7:1, at least 2.8:1, at least 2.9:1, or at least 3:1 by weight.

Inventive concept 17. The method of any one of inventive concepts 11 to 16, wherein the ratio of ethanol to water in the mixture is not more than 4:1, not more than 3.9:1, not more than 3.8:1, not more than 3.7:1, not more than 3.6:1, not more than 3.5:1, not more than 3.4:1, not more than 3.3:1, not more than 3.2:1, or not more than 3.1:1 by weight.

Inventive concept 18. The method of any one of inventive concepts 11 to 17, wherein the mixture of ethanol and water contains NaOH in a concentration of 0.01 to 0.125 molar.

Inventive concept 19. The method of inventive concept 18, wherein the concentration of NaOH is at least 0.02 M, at least 0.03 M, at least 0.04 M, at least 0.05 M, at least 0.06 M, at least 0.07 M, at least 0.08 M, at least 0.09 M, at least 1.0 M, at least 1.1 M or at least 1.2 M.

Inventive concept 20. The method of any one of inventive concepts 11 to 17, wherein the mixture of ethanol and water contains HCl in a concentration of 0.01 to 0.25 molar.

Inventive concept 21. The method of inventive concept 20, wherein the concentration of HCl is at least 0.1 molar, at least 0.2 molar, at least 0.3 molar, at least 0.4 molar, at least 0.5 molar, at least 0.6 molar, at least 0.7 molar, at least 0.8 molar, at least 0.9 molar, at least 1.0 molar, at least 1.1 molar, at least 1.2 molar, or at least 0.125 molar.

Inventive concept 22. The method of any one of inventive concepts 11 to 21, wherein the ratio of the mixture of ethanol and water to copaiba resin is at least 3:1 by weight.

Inventive concept 23. The method of inventive concept 23, wherein the ratio of the mixture of ethanol and water to copaiba resin is at least 3.5:1, at least 4:1, at least 4.5:1, at least 5:1, at least 5.5:1 or at least 6:1 by weight.

Inventive concept 24. The method of any one of inventive concepts 11 to 23, wherein the method further comprises removing at least some of the water and ethanol from the collected upper fraction.

Inventive concept 25. The method of any one of inventive concepts 11 to 24, wherein the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (when present), crolechinic acid, hardwickiic acid, kolavenic acid and copalic acid, taken together, to said BCP in said upper fraction is at least 1:1 by weight.

Inventive concept 26. The method of inventive concept 25, wherein the ratio of said 7-alpha-acetoxyhardwickiic acid, crolechinic acid, hardwickiic acid, kolavenic acid and copalic acid, taken together, to said BCP in said upper fraction is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1 or at least 2.5:1 by weight.

Inventive concept 27. The method of any one of inventive concepts 11 to 26, wherein the method further comprises chromatographically separating residual BCP from the diterpenes present in the upper fraction and collecting the diterpenes.

There is also provided, in accordance with an inventive concept 28, a method of preparing a composition which is active against spores of *Alicyclobacillus* and has a reduced concentration of beta-caryophyllene (BCP) relative to the concentration of BCP in copaiba resin obtained from *Copaifera*, the method comprising extracting resin obtained from *Copaifera* with a mixture of water and ethanol, and collecting the upper fraction obtained from the extraction. In this context, the term "active against spores of *Alicyclobacillus*" means that, when added at a concentration of 5 μg/ml to a sample of apple juice having a turbidity of not more than 1 Nephelometric Turbidity Units (NTU) as measured in accordance with EPA standard 180.1 (published August 1993), and containing $10^4$ spores of *Alicyclobacillus*/ml and maintained thereafter at 37° C., the composition prevents regrowth of *Alicyclobacillus* for at least four days, as determined by optical density measurement at 600 nm.

Inventive concept 29. The method of inventive concept 28, wherein the copaiba resin is obtained from *Copaifera officinalis*.

Inventive concept 30. The method of inventive concept 28 or 29, wherein the composition is active against spores of *Alicyclobacillus* acidoterrestris.

Inventive concept 31. The method of any one of inventive concepts 28 to 30, wherein the ratio of ethanol to water in the mixture is at least 1:1 by weight.

Inventive concept 32. The method of inventive concept 31, wherein the ratio of ethanol to water in the mixture is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7:1, at least 2.8:1, at least 2.9:1, or at least 3:1 by weight.

Inventive concept 33. The method of any one of inventive concepts 28 to 32, wherein the ratio of ethanol to water in the mixture is not more than 4:1, not more than 3.9:1, not more than 3.8:1, not more than 3.7:1, not more than 3.6:1, not more than 3.5:1, not more than 3.4:1, not more than 3.3:1, not more than 3.2:1, or not more than 3.1:1 by weight.

Inventive concept 34. The method of any one of inventive concepts 28 to 33, wherein the mixture of ethanol and water contains NaOH in a concentration of 0.01 to 0.125 molar.

Inventive concept 35. The method of inventive concept 34, wherein the concentration of NaOH is at least 0.02 M, at least 0.03 M, at least 0.04 M, at least 0.05 M, at least 0.06 M, at least 0.07 M, at least 0.08 M, at least 0.09 M, at least 1.0M, at least 1.1 M or at least 1.2 M.

Inventive concept 36. The method of any one of inventive concepts 28 to 33, wherein the mixture of ethanol and water contains HCl in a concentration of 0.01 to 0.25 molar.

Inventive concept 37. The method of inventive concept 36, wherein the concentration of HCl is at least 0.1 molar, at least 0.2 molar, at least 0.3 molar, at least 0.4 molar, at least 0.5 molar, at least 0.6 molar, at least 0.7 molar, at least 0.8 molar, at least 0.9 molar, at least 1.0 molar, at least 1.1 molar, at least 1.2 molar, or at least 0.125 molar.

Inventive concept 38, The method of any one of inventive concepts 28 to 37, wherein the ratio of the mixture of ethanol and water to copaiba resin is at least 3:1 by weight.

Inventive concept 39. The method of inventive concept 38, wherein the ratio of the mixture of ethanol and water to copaiba resin is at least 3.5:1, at least 4:1, at least 4.5:1, at least 5:1, at least 5.5:1 or at least 6:1 by weight.

Inventive concept 40. The method of any one of inventive concepts 28 to 39, wherein the method further comprises removing at least some of the water and ethanol from the collected upper fraction.

Inventive concept 41. The method of any one of inventive concepts 28 to 40, wherein the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (if present), crolechinic acid, hardwickiic acid, kolavenic acid and copalic acid, taken together, to said BCP in said upper fraction is at least 1:1 by weight.

Inventive concept 42. The method of inventive concept 41, wherein the ratio of said 7-alpha-acetoxyhardwickiic acid (if present), crolechinic acid, hardwickiic acid, kolavenic acid and copalic acid, taken together, to said BCP in said upper fraction is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1 or at least 2.5:1 by weight.

Inventive concept 43. The method of any one of inventive concepts 28 to 42, wherein the method further comprises chromatographically separating residual BCP from the diterpenes present in the upper fraction and collecting the diterpenes.

There is also provided, in accordance with an inventive concept 44, a composition of matter, prepared by extraction as described herein, i.e. by a method comprising extracting resin obtained from *Copaifera* with a mixture of water and ethanol, and collecting the upper fraction obtained from the extraction.

Inventive concept 45. The composition of inventive concept 44, wherein the composition is active against spores of *Alicyclobacillus*.

Inventive concept 46. The composition of inventive concept 44 or 45, wherein the composition has a reduced concentration of beta-caryophyllene (BCP) relative to the concentration of BCP in copaiba resin obtained from *Copaifera*.

Inventive concept 47. The composition of any one of inventive concepts 44 to 46, wherein the copaiba resin is obtained from *Copaifera officinalis*.

Inventive concept 48. The composition of any one of inventive concepts 44 to 47, wherein the composition is active against spores of *Alicyclobacillus acidoterrestris*.

Inventive concept 49, The composition of any one of inventive concepts 44 to 48, wherein the ratio of ethanol to water in the mixture is at least 1:1 by weight.

Inventive concept 50. The composition of inventive concept 49, wherein the ratio of ethanol to water in the mixture is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 2.6:1, at least 2.7:1, at least 2.8:1, at least 2.9:1, or at least 3:1 by weight.

Inventive concept 51. The composition of any one of inventive concepts 44 to 50, wherein the ratio of ethanol to water in the mixture is not more than 4:1, not more than 3.9:1, not more than 3.8:1, not more than 3.7:1, not more than 3.6:1, not more than 3.5:1, not more than 3.4:1, not more than 3.3:1, not more than 3.2:1, or not more than 3.1:1 by weight.

Inventive concept 52. The composition of any one of inventive concepts 44 to 51, wherein the mixture of ethanol and water contains NaOH in a concentration of 0.01 to 0.125 molar.

Inventive concept 53. The composition of inventive concept 52, wherein the concentration of NaOH is at least 0.02 M, at least 0.03 M, at least 0.04 M, at least 0.05 M, at least 0.06 M, at least 0.07 M, at least 0.08 M, at least 0.09 M, at least 1.0 M, at least 1.1 M or at least 1.2 M.

Inventive concept 54. The composition of any one of inventive concepts 44 to 51, wherein the mixture of ethanol and water contains HCl in a concentration of 0.01 to 0.25 molar.

Inventive concept 55. The composition of any inventive concept 54, wherein the concentration of HCl is at least 0.1 molar, at least 0.2 molar, at least 0.3 molar, at least 0.4 molar, at least 0.5 molar, at least 0.6 molar, at least 0.7 molar, at least 0.8 molar, at least 0.9 molar, at least 1.0 molar, at least 1.1 molar, at least 1.2 molar, or at least 0.125 molar.

Inventive concept 56, The composition of any one of inventive concepts 44 to 55, wherein the ratio of the mixture of ethanol and water to copaiba resin is at least 3:1 by weight.

Inventive concept 57, The composition of inventive concept 56, wherein the ratio of the mixture of ethanol and water to copaiba resin is at least 3.5:1, at least 4:1, at least 4.5:1, at least 5:1, at least 5.5:1 or at least 6:1 by weight.

Inventive concept 58. The composition of any one of inventive concepts 44 to 57, wherein the method further comprises removing at least some of the water and ethanol from the collected upper fraction.

Inventive concept 59. The composition of any one of inventive concepts 44 to 58, wherein the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (if present), crolechinic acid, hardwickiic acid, kolavenic acid and copalic acid, taken together, to said BCP in said upper fraction is at least 1:1 by weight.

Inventive concept 60. The composition of inventive concept 59, wherein the ratio of said 7-alpha-acetoxyhardwickiic acid (if present), crolechinic acid, hardwickiic acid, kolavenic acid and copalic acid, taken together, to said BCP in said upper fraction is at least 1.1:1, at least 1.2:1, at least 1.3:1, at least 1.4:1, at least 1.5:1, at least 1.6:1, at least 1.7:1, at least 0.1.8:1, at least 1.9:1, at least 2:1, at least 2.1:1, at least 2.2:1, at least 2.3:1, at least 2.4:1 or at least 2.5:1 by weight.

Inventive concept 61. The composition of any one of inventive concepts 44 to 60, wherein the method further comprises chromatographically separating residual BCP from the diterpenes present in the upper fraction and collecting the diterpenes.

Inventive concept 61.1. The composition of any one of inventive concepts 44 to 60 wherein the composition is substantially free of hexane and dichloromethane.

There is also provided, in accordance with inventive concept 62, a method, the method comprising adding to a beverage a composition comprising (a) crolechinic acid, hardwickiic acid, kolavenic acid and copalic acid, and, optionally, 7-alpha-acetoxyhardwickiic acid, and (b) optionally, beta-caryophyllene.

Inventive concept 63. The method of inventive concept 62, wherein the composition is a composition as recited in any one of inventive concepts 1 to 0.10 or 44 to 61.1.

Inventive concept 64. The method of inventive concept 62 or 63, wherein the beverage has a turbidity of not more than 5 Nephelometric Turbidity Units (NTU), as measured in accordance with the United States Environmental Protection Agency Method no. 180.1, published August 1993.

Inventive concept 65. The method of any one of inventive concepts 62 to 64, wherein the beverage has a turbidity of not more than 4 NTU.

Inventive concept 66. The method of any one of inventive concepts 62 to 65, wherein the beverage has a turbidity of not more than 3 NTU.

Inventive concept 67. The method of any one of inventive concepts 62 to 66, wherein the beverage has a turbidity of not more than 2 NTU.

Inventive concept 68. The method of any one of inventive concepts 62 to 67, wherein the beverage has a turbidity of not more than 1 NTU.

Inventive concept 69. The method of any one of inventive concepts 62 to 68, wherein the method is for enhancing the efficacy of pasteurization of the beverage.

Inventive concept 70. The method of any one of inventive concepts 62 to 69, wherein the composition is active against spores of *Alicyclobacillus*.

Inventive concept 71. The method of inventive concept 70, wherein the composition is active against spores of *Alicyclobacillus acidoterrestris*.

Inventive concept 72. The method of any one of inventive concepts 62 to 71, wherein the composition has a reduced concentration of beta-caryophyllene (BCP) relative to the concentration of BCP in copaiba resin obtained from *Copaifera*.

Inventive concept 73. The method of any one of inventive concepts 62 to 72, wherein the copaiba resin is from *Copaifera officinalis*.

Inventive concept 74. The method of any one of inventive concepts 62 to 73, wherein the ratio of 7-alpha-acetoxyhardwickiic acid (if present), crolechinic acid, hardwickiic acid, kolavenic acid and copalic acid, taken together, to the beta-caryophyllene, when beta-caryophyllene is present, is at least 1:1 by weight.

Inventive concept 75. The method of any one of inventive concepts 62 to 74, wherein the composition is added to the beverage at concentration of at least 1.25 microgram composition per ml beverage.

Inventive concept 76, The method of inventive concept 75, wherein the composition is added to the beverage at a concentration of at least 2.5 microgram composition per ml beverage.

Inventive concept 77. The method of inventive concept 76, wherein the composition is added to the beverage at a concentration of at least 3.75 microgram composition per ml beverage.

Inventive concept 78. The method of inventive concept 77, wherein the composition is added to the beverage at a concentration of at least 5.0 microgram composition per ml beverage.

Inventive concept 79. The method of any one of inventive concepts 62 to 78, wherein the composition is added to the beverage at a concentration of not more than 5.0 microgram composition per ml beverage.

Inventive concept 80. The method of any one of inventive concepts 62 to 79, wherein the composition is allowed to contact the beverage for at least two days, at least three days, at least four days, or at least five days.

Inventive concept 81. The method of any one of inventive concepts 62 to 80, wherein the composition is added to the beverage prior to pasteurization.

Inventive concept 82. The method of any one of inventive concepts 62 to 80, wherein the composition is added to the beverage after pasteurization.

Inventive concept 83. The method of any one of inventive concepts 62 to 82, wherein the beverage is acidic.

Inventive concept 84. The method of inventive concept 83, wherein the beverage has a pH in the range of 3 to 6.

Inventive concept 85. The method of any one of inventive concepts 62 to 84, wherein the beverage is a fruit juice.

Inventive concept 86. The method of inventive concept 85, wherein the fruit juice is apple juice.

Inventive concept 87. The method of inventive concept 85, wherein the fruit juice is grape juice.

Inventive concept 88. The method of inventive concept 85, wherein the fruit juice is peach juice.

Inventive concept 89. The method of inventive concept 85, wherein the fruit juice is watermelon juice.

Inventive concept 90. The method of inventive concept 85, wherein the fruit juice is clear orange juice.

Inventive concept 91. The method of any one of inventive concepts 62 to 90, wherein the composition has been prepared by a method of any one of inventive concepts 11 to 43.

There is also provided, in accordance with an inventive concept 92, a method comprising adding to a beverage a composition which has been prepared by extracting *Copaifera* resin with a mixture of water and ethanol, and collecting the upper fraction obtained from the extraction to obtain the composition.

Inventive concept 93. The method of inventive concept 92, wherein the beverage has a turbidity of not more than 5 Nephelometric Turbidity Units (NTU), as measured in accordance with the United States Environmental Protection Agency Method no. 180.1, published August 1993.

Inventive concept 94, The method of inventive concept 93, wherein the beverage has a turbidity of not more than 4 NTU.

Inventive concept 95. The method of inventive concept 94, wherein the beverage has a turbidity of not more than 3 NTU.

Inventive concept 96. The method of inventive concept 95, wherein the beverage has a turbidity of not more than 2 NTU.

Inventive concept 97. The method of inventive concept 96, wherein the beverage has a turbidity of not more than 1 NTU.

Inventive concept 98. The method of any one of inventive concepts 92 to 97, wherein the method is for enhancing the efficacy of pasteurization of the beverage.

Inventive concept 99. The method of any one of inventive concepts 92 to 97, wherein the method is for controlling the growth of Gram-positive bacteria, including spores of Gram-positive bacteria, in the beverage.

Inventive concept 100, The method of any one of inventive concepts 92 to 99, wherein the composition is active against spores of *Alicyclobacillus acidoterrestris*.

Inventive concept 101. The method of any one of inventive concepts 92 to 100, wherein the composition has a reduced concentration of beta-caryophyllene (BCP) relative to the concentration of BCP in copaiba resin obtained from *Copaifera*.

Inventive concept 102. The method of any one of inventive concepts 92 to 101, wherein the copaiba resin is from *Copaifera officinalis*.

Inventive concept 103. The method of any one of inventive concepts 92 to 102, wherein the composition comprises (a) crolechinic acid, hardwickiic acid, kolavenic acid copalic acid, and, optionally, 7-alpha-acetoxyhardwickiic acid, and (b) optionally, beta-caryophyllene.

Inventive concept 104. The method of inventive concept 103, wherein the ratio of 7-alpha-acetoxyhardwickiic acid (if present), crolechinic acid, hardwickiic acid, kolavenic acid and copalic acid, taken together, to the beta-caryophyllene, when beta-caryophyllene is present, is at least 1:1 by weight.

Inventive concept 105. The method of any one of inventive concepts 92 to 104, wherein the composition is added to the beverage at concentration of at least 1.25 microgram composition per ml beverage.

Inventive concept 106. The method of inventive concept 105, wherein the composition is added to the beverage at a concentration of at least 2.5 microgram composition per ml beverage.

Inventive concept 107. The method of inventive concept 106, wherein the composition is added to the beverage at a concentration of at least 3.75 microgram composition per ml beverage.

Inventive concept 108. The method of inventive concept 107, wherein the composition is added to the beverage at a concentration of at least 5.0 microgram composition per ml beverage.

Inventive concept 109. The method of any one of inventive concepts 92 to 108, wherein the composition is added to the beverage at a concentration of not more than 5.0 microgram composition per ml beverage.

Inventive concept 110. The method of any one of inventive concepts 92 to 109, wherein the composition is allowed to contact the beverage for at least two days, at least three days, at least four days, or at least five days.

Inventive concept 111. The method of any one of inventive concepts 92 to 110, wherein the composition is added to the beverage prior to pasteurization.

Inventive concept 112. The method of any one of inventive concepts 92 to 110, wherein the composition is added to the beverage after pasteurization.

Inventive concept 113. The method of any one of inventive concepts 92 to 112, wherein the beverage is acidic.

Inventive concept 114. The method of any one of inventive concepts 92 to 113, wherein the beverage is fruit juice.

Inventive concept 115. The method of inventive concept 114, wherein the fruit juice is apple juice.

Inventive concept 116. The method of inventive concept 114, wherein the fruit juice is grape juice.

Inventive concept 117. The method of inventive concept 114, wherein the fruit juice is peach juice.

Inventive concept 118. The method of inventive concept 114, wherein the fruit juice is watermelon juice.

Inventive concept 119. The method of inventive concept 114, wherein the fruit juice is clear orange juice.

Inventive concept 120. The method of any one of inventive concepts 92 to 119, wherein the composition is a composition of any one of inventive concepts 1 to 10 or 44 to 61.1.

Inventive concept 121. The method of any one of inventive concepts 92 to 120, wherein the composition has been prepared by a method a method of any one of inventive concepts 11 to 43.

There is also provided, in accordance with an inventive concept 122, a beverage in a container, the beverage containing a composition comprising (a) crolechinic acid, hardwickiic acid, kolavenic acid, copalic acid, and, optionally, 7-alpha-acetoxyhardwickiic acid, and (b) optionally, beta-caryophyllene according to any one of inventive concepts 1 to 10 or 44 to 61.1.

Inventive concept 122.1. The beverage of inventive concept 122, wherein the composition comprises 7-alpha-acetoxyhardwickiic acid.

Inventive concept 123. The beverage of inventive concept 122 or 122.1 wherein the beverage is a clear beverage.

Inventive concept 124. The beverage of any one of inventive concepts 122 to 123, wherein the beverage has a turbidity of not more than 5 Nephelometric Turbidity Units (NTU), as measured in accordance with the United States Environmental Protection Agency Method no. 180.1, published August 1993.

Inventive concept 125. The beverage of inventive concept 0.124, wherein the beverage has a turbidity of not more than 4 NTU.

Inventive concept 126. The beverage of inventive concept 125, wherein the beverage has a turbidity of not more than 3 NTU.

Inventive concept 127. The beverage of inventive concept 126, wherein the beverage has a turbidity of not more than 2 NTU.

Inventive concept 128. The beverage of inventive concept 127, wherein the beverage has a turbidity of not more than 1 NTU.

Inventive concept 129. The beverage of any one of inventive concepts 122 to 128, wherein the composition is present in the beverage at concentration of at least 1.25 microgram composition per ml beverage.

Inventive concept 130. The beverage of inventive concept 129, wherein the composition is present in the beverage at a concentration of at least 2.5 microgram composition per mi beverage.

Inventive concept 131. The beverage of inventive concept 130, wherein the composition is present in the beverage at a concentration of at least 3.75 microgram composition per ml beverage.

Inventive concept 132. The beverage of inventive concept 131, wherein the composition is present in the beverage at a concentration of at least 5.0 microgram composition per ml beverage.

Inventive concept 133. The beverage of any one of inventive concepts 122 to 132, wherein the composition is present in the beverage at a concentration of not more than 5.0 microgram composition per ml beverage.

Inventive concept 134. The beverage of any one of inventive concepts 122 to 133, wherein the beverage is acidic.

Inventive concept 134.1. The beverage of any one of inventive concepts 122 to 134, wherein the beverage is a fruit juice.

Inventive concept 135, The beverage of inventive concept 134.1, wherein the fruit juice is apple juice.

Inventive concept 136. The beverage of inventive concept 134.1, wherein fruit juice is grape juice.

Inventive concept 136.1. The beverage of inventive concept 134.1, wherein the fruit juice is peach juice.

Inventive concept 137. The beverage of inventive concept 134.1, wherein the fruit juice is watermelon juice.

Inventive concept 138, The beverage of inventive concept 134.1, wherein the fruit juice is clear orange juice.

Inventive concept 139. The beverage of any one of inventive concepts 122 to 138, wherein the composition is a composition according to any one of inventive concepts 1 to 10 or 44 to 61.1.

Inventive concept 140. The beverage of any one of inventive concepts 122 to 139, wherein the composition has been prepared by a method a method of any one of inventive concepts 11 to 43.

There is also provided, in accordance with an inventive concept 141, a beverage in a container, the beverage containing a composition prepared by extracting *Copaifera* resin with a mixture of water and ethanol, and collecting the upper fraction obtained from the extraction to obtain the composition.

Inventive concept 142. A beverage according to inventive concept 141, wherein the composition comprises (a) crolechinic acid, hardwickiic acid, kolavenic acid, copalic acid, and, optionally, 7-alpha-acetoxyhardwickiic acid, and (b) optionally, beta-caryophyllene.

Inventive concept 143. A beverage according to inventive concept 141 or 142, wherein the composition comprises 7-alpha-acetoxyhardwickiic acid.

Inventive concept 143.1. A beverage according to any one of inventive concepts 141 to 143, wherein the beverage has a turbidity of not more than 5 Nephelometric Turbidity Units (NTU), as measured in accordance with the United States Environmental Protection Agency Method no. 180.1, published August 1993.

Inventive concept 143.2. The beverage of inventive concept 143.1 which has a turbidity of not more than 4 NTU.

Inventive concept 143.3. The beverage of inventive concept 143.2 which has a turbidity of not more than 3 NTU.

Inventive concept 143.4. The beverage of inventive concept 143.3 which has a turbidity of not more than 2 NTU.

Inventive concept 143.5, The beverage of inventive concept 143.4 which has a turbidity of not more than 1 NTU.

Inventive concept 144. A beverage according to any one of inventive concepts 141 to 143.5, wherein the composition is present in the beverage at concentration of at least 1.25 microgram composition per ml beverage.

Inventive concept 145. A beverage according to inventive concept 144, wherein the composition is present in the beverage at a concentration of at least 2.5 microgram composition per ml beverage.

Inventive concept 146. A beverage according to inventive concept 145, wherein the composition is present in the beverage at a concentration of at least 3.75 microgram composition per ml beverage.

Inventive concept 147, A beverage according to inventive concept 146, wherein the composition is present in the beverage at a concentration of at least 5.0 microgram composition per ml beverage.

Inventive concept 148, A beverage according to any one of inventive concepts 141 to 147, wherein the composition is present in the beverage at a concentration of not more than 5.0 microgram composition per ml beverage.

Inventive concept 149. A beverage according to any one of inventive concepts 141 to 148, wherein the beverage is acidic.

Inventive concept 150. A beverage according to any one of inventive concepts 141 to 149, wherein the beverage is a fruit juice.

Inventive concept 151. A beverage according to inventive concept 150, wherein the fruit juice is apple juice.

Inventive concept 152. A beverage according to inventive concept 150, wherein the fruit juice is grape juice.

Inventive concept 153. A beverage according to inventive concept 150, wherein the fruit juice is peach juice.

Inventive concept 154. A beverage according to inventive concept 150, wherein the fruit juice is watermelon juice.

Inventive concept 155. A beverage according to inventive concept 150, wherein the fruit juice is clear orange juice.

Inventive concept 156. The beverage of any one of inventive concepts 141 to 155, wherein the composition is a composition according to any one of inventive concepts 1 to 10 or 44 to 61.1.

Inventive concept 157. The beverage of any one of inventive concepts 141 to 156, wherein the composition has been prepared by a method a method of any one of inventive concepts 11 to 43.

There is also provided, in accordance with an inventive concept 158, a method of controlling the growth of Gram-positive bacteria, including spores of Gram-positive bacteria, in a beverage, comprising adding to the beverage a composition comprising (a) crolechinic acid, hardwickiic acid, kolavenic acid copalic acid, and, optionally, 7-alpha-acetoxyhardwickiic acid, and (b) optionally, beta-caryophyllene.

Inventive concept 159. The method of inventive concept 158, wherein the composition is added to the beverage at concentration of at least 1.25 microgram composition per ml beverage.

Inventive concept 160. The method of inventive concept 159, wherein the composition is added to the beverage at a concentration of at least 2.5 microgram composition per ml beverage.

Inventive concept 161. The method of inventive concept 160, wherein the composition is added to the beverage at a concentration of at least 3.75 microgram composition per ml beverage.

Inventive concept 162. The method of inventive concept 161, wherein the composition is added to the beverage at a concentration of at least 5.0 microgram composition per ml beverage.

Inventive concept 163. The method of any one of inventive concepts 158 to 162, wherein the composition is added to the beverage at a concentration of not more than 5.0 microgram composition per ml beverage.

Inventive concept 164. The method of any one of inventive concepts 158 to 163, wherein the composition is allowed to contact the beverage for at least two days, at least three days, at least four days, or at least five days.

Inventive concept 165. The method of any one of inventive concepts 158 to 164, wherein the composition is added to the beverage prior to pasteurization.

Inventive concept 166. The method of any one of inventive concepts 158 to 164, wherein the composition is added to the beverage after pasteurization.

Inventive concept 167. The method of any one of inventive concepts 158 to 166, wherein the beverage is acidic.

Inventive concept 168. The method of any one of inventive concepts 158 to 167, wherein the beverage is a fruit juice.

Inventive concept 169. The method of inventive concept 168, wherein the fruit juice is apple juice.

Inventive concept 170. The method of inventive concept 168, wherein the fruit juice is grape juice.

Inventive concept 171. The method of inventive concept 168, wherein the fruit juice is peach juice.

Inventive concept 172. The method of inventive concept 168, wherein the fruit juice is watermelon juice.

Inventive concept 173. The method of inventive concept 168, wherein the fruit juice is clear orange juice.

Inventive concept 173.1. A beverage according to any one of inventive concepts 158 to 173, wherein the beverage has a turbidity of not more than 5 Nephelometric Turbidity Units (NTU), as measured in accordance with the United States Environmental Protection Agency Method no. 180.1, published August 1993.

Inventive concept 173.2. The beverage of inventive concept 173.1 which has a turbidity of not more than 4 NTU.

Inventive concept 173.3. The beverage of inventive concept 173.2 which has a turbidity of not more than 3 NTU.

Inventive concept 173.4. The beverage of inventive concept 173.3 which has a turbidity of not more than 2 NTU.

Inventive concept 173.5, The beverage of inventive concept 173.4 which has a turbidity of not more than 1 NTU.

Inventive concept 174. The method of any one of inventive concepts 158 to 173.5, wherein the composition is a composition according to any one of inventive concepts 1-10 or 44 to 61.1.

Inventive concept 175. The method of any one of inventive concepts 158 to 174, wherein the composition has been prepared by a method of any one of inventive concepts 11 to 43.

The invention claimed is:

1. A composition of matter comprising (a) crolechinic acid, hardwickiic acid, kolavenic acid, copalic acid, and, optionally, 7-alpha-acetoxyhardwickiic acid, and (b) beta-caryophyllene (BCP), the ratio of said crolechinic acid, hardwickiic acid, kolavenic acid, copalic acid, and 7-alpha-acetoxyhardwickiic acid if present, taken together, to said beta-caryophyllene, being at least 1.1:1 by weight, and wherein the composition is substantially free of hexane and dichloromethane.

2. The composition of claim 1, wherein at least one of the following is true:
   (i) the ratio of the crolechinic acid, hardwickiic acid, kolavenic acid, copalic acid, and 7-alpha-acetoxyhardwickiic acid, if present, taken together, to the beta-caryophyllene is at least 1.2:1 by weight,
   (ii) the ratio of the crolechinic acid, hardwickiic acid, kolavenic acid, copalic acid, and 7-alpha-acetoxyhardwickiic acid, if present, taken together, to the beta-caryophyllene is not greater than 100:1 by weight.

3. The composition of claim 1, wherein the composition is active against spores of *Alicyclobacillus*.

4. A method of preparing a composition, which composition has, relative to the concentration of crolechinic acid, hardwickiic acid, kolavenic acid, copalic acid, if present, 7-alpha-acetoxyhardwickiic acid, taken together in copaiba resin obtained from *Copaifera*, a reduced concentration of beta-caryophyllene (BCP), the method comprising extracting resin obtained from *Copaifera* with a mixture of water and ethanol, whereby to obtain an upper fraction and lower fraction, and collecting the upper fraction obtained from the extraction, whereby to obtain the composition; and, optionally, further comprising removing at least some of the water and ethanol from the collected upper fraction.

5. The method of claim 4, wherein the copaiba resin is obtained from *Copaifera officinalis*.

6. The method of claim 4, wherein at least one of the following is true:
   (1) the ratio of ethanol to water in the mixture is at least by weight;
   (2) the ratio of ethanol to water in the mixture is not more than 4:1 by weight;
   (3) the mixture of ethanol and water contains (a) NaOH in a concentration of 0.01 to 0.125 molar, or (b) HCl in a concentration of 0.01 to 0.25 molar;
   (4) the ratio of the mixture of ethanol and water to copaiba resin is at least 3:1 by weight;
   (5) the upper fraction contains crolechinic acid, hardwickiic acid, kolavenic acid, copalic acid, and, optionally, 7-alpha-acetoxyhardwickiic acid, and the ratio of said 7-alpha-acetoxyhardwickiic acid (when present), crolechinic acid, hardwickiic acid, kolavenic acid and copalic acid, taken together, to said BCP in said upper fraction is at least 1.1:1 by weight.

7. The composition of claim 2, wherein the composition is active against spores of *Alicyclobacillus*.

8. The method of claim 4, wherein at least one of the following is true:
   (i) the composition is a composition of claim 1, wherein the composition has, relative to the concentration of crolechinic acid, hardwickiic acid, kolavenic acid, copalic acid and, if present 7-alpha-acetoxyhardwickiic acid, taken together in copaiba resin obtained from *Copaifera*, a reduced concentration of beta-caryophyllene (BCP);
   (ii) the composition is a composition of claim 2, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (iii) the composition is a composition of claim 3, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (iv) the composition is a composition of claim 7, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (v) the composition is active against spores of *Alicyclobacillus* and has a reduced concentration of beta-caryophyllene (BCP) relative to the concentration of BCP in copaiba resin obtained from *Copaifera*.

9. The method of claim 5, wherein at least one of the following is true:
   (i) the composition is a composition of claim 1, wherein the composition has, relative to the concentration of crolechinic acid, hardwickiic acid, kolavenic acid, copalic and, if present, 7-alpha-acetoxyhardwickiic acid, acid taken together in copaiba resin obtained from *Copaifera*, a reduced concentration of beta-caryophyllene (BCP);
   (ii) the composition is a composition of claim 2, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (iii) the composition is a composition of claim 3, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);

(iv) the composition is a composition of claim 7, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);

(v) the composition is active against spores of *Alicyclobacillus* and has a reduced concentration of beta-caryophyllene (BCP) relative to the concentration of BCP in copaiba resin obtained from *Copaifera*.

10. The method of claim 6, wherein at least one of the following is true:
   (i) the composition is a composition of claim 1, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (ii) the composition is a composition of claim 2, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (iii) the composition is a composition of claim 3, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (iv) the composition is a composition of claim 7, wherein the composition has, relative to the concentration of crolechinic acid, hardwickiic acid, kolavenic acid, copalic acid and, if present, 7-alpha-acetoxyhardwickiic acid, taken together in copaiba resin obtained from *Copaifera*, a reduced concentration of beta-caryophyllene (BCP);
   (v) the composition is active against spores of *Alicyclobacillus* and has a reduced concentration of beta-caryophyllene (BCP) relative to the concentration of BCP in copaiba resin obtained from *Copaifera*.

11. A beverage in a container, the beverage containing a composition wherein at least one of the following is true:
   (i) the composition comprises (a) crolechinic acid, hardwickiic acid, kolavenic acid, copalic acid, and, optionally, 7-alpha-acetoxyhardwickiic acid, and (b) beta-caryophyllene, the ratio of said crolechinic acid, hardwickiic acid, kolavenic acid, copalic acid, and 7-alpha-acetoxyhardwickiic acid if present, taken together, to said beta-caryophyllene being at least 1.1:1 by weight;
   (ii) the composition has been prepared by extracting *Copaifera* resin with a mixture of water and ethanol, whereby to obtain an upper fraction and lower fraction, and collecting the upper fraction obtained from the extraction to obtain the composition.

12. The beverage of claim 11, wherein the beverage has a turbidity of not more than 5 Nephelometric Turbidity Units (NTU), not more than 4 NTU, not more than 3 NTU, not more than 2 NTU, or not more than 1 NTU, as measured in accordance with the United States Environmental Protection Agency Method no. 180.1, published August 1993.

13. The beverage of claim 11, wherein the composition is present in the beverage (a) at concentration of at least 1.25 microgram composition per ml beverage, and/or (b) a concentration of not more than 5.0 microgram composition per ml beverage.

14. The beverage of claim 11, wherein the beverage is acidic and/or a fruit juice, optionally selected from the group consisting of apple juice, grape juice, peach juice, and watermelon juice.

15. The beverage of claim 11, wherein at least one of the following is true: (i) the composition is a composition according to claim 1; (ii) the composition is a composition according to claim 2; (iii) the composition is a composition according to claim 3; (iv) the composition is a composition according to claim 7; (v) the composition has been prepared by the method claim 4; (vi) the composition has been prepared by the method of claim 5; (vii) the composition has been prepared by the method of claim 5; (viii) the composition has been prepared by the method of claim 8; (ix) the composition has been prepared by the method of claim 9; (x) the composition has been prepared by the method of claim 10.

16. The beverage of claim 12, wherein the composition is present in the beverage (a) at concentration of at least 1.25 microgram composition per ml beverage and/or (b) a concentration of not more than 5.0 microgram composition per ml beverage.

17. The beverage of claim 12, wherein the beverage is acidic and/or a fruit juice, optionally selected from the group consisting of apple juice, grape juice, peach juice, and watermelon juice.

18. The beverage of claim 13, wherein the beverage is acidic and/or a fruit juice, optionally selected from the group consisting of apple juice, grape juice, peach juice, and watermelon juice.

19. The beverage of claim 12, wherein at least one of the following is true: (i) the composition is a composition according to claim 1; (ii) the composition is a composition according to claim 2; (iii) the composition is a composition according to claim 3; (iv) the composition is a composition according to claim 7; (v) the composition has been prepared by the method claim 4; (vi) the composition has been prepared by the method of claim 5; (vii) the composition has been prepared by the method of claim 5; (viii) the composition has been prepared by the method of claim 8; (ix) the composition has been prepared by the method of claim 9; (x) the composition has been prepared by the method of claim 10.

20. The beverage of claim 13, wherein at least one of the following is true: (i) the composition is a composition according to claim 1; (ii) the composition is a composition according to claim 2; (iii) the composition is a composition according to claim 3; (iv) the composition is a composition according to claim 7; (v) the composition has been prepared by the method claim 4; (vi) the composition has been prepared by the method of claim 5; (vii) the composition has been prepared by the method of claim 5; (viii) the composition has been prepared by the method of claim 8; (ix) the composition has been prepared by the method of claim 9; (x) the composition has been prepared by the method of claim 10.

* * * * *